(12) United States Patent
Boyanov et al.

(10) Patent No.: US 11,782,006 B2
(45) Date of Patent: Oct. 10, 2023

(54) SENSING SYSTEMS

(71) Applicant: ILLUMINA, INC., San Diego, CA (US)

(72) Inventors: Boyan Boyanov, San Diego, CA (US); Sergio Peisajovich, San Diego, CA (US); Jeffrey G. Mandell, Rancho Santa Fe, CA (US)

(73) Assignee: Illumina, Inc., San Diego, CA (US)

(*) Notice: Subject to any disclaimer, the term of this patent is extended or adjusted under 35 U.S.C. 154(b) by 563 days.

(21) Appl. No.: 16/701,747

(22) Filed: Dec. 3, 2019

(65) Prior Publication Data
US 2020/0200693 A1 Jun. 25, 2020

Related U.S. Application Data

(60) Provisional application No. 62/783,951, filed on Dec. 21, 2018.

(51) Int. Cl.
*G01N 27/12* (2006.01)
*G01N 27/414* (2006.01)
(Continued)

(52) U.S. Cl.
CPC ............ *G01N 27/125* (2013.01); *C12Q 1/68* (2013.01); *G01N 27/128* (2013.01); *G01N 27/4145* (2013.01); *G01N 33/54366* (2013.01)

(58) Field of Classification Search
CPC ............... G01N 27/125; G01N 27/128; G01N 27/4145; G01N 33/54366; C12Q 1/68
See application file for complete search history.

(56) References Cited

U.S. PATENT DOCUMENTS

| 8,003,374 B2 | 8/2011 | Heeger et al. |
| 9,809,852 B2 | 11/2017 | Esfandyarpour et al. |

(Continued)

FOREIGN PATENT DOCUMENTS

| EA | 022475 B1 | 1/2016 |
| RU | 2198221 C2 | 2/2003 |

(Continued)

OTHER PUBLICATIONS

Maehashi, et al., "Label-Free Protein Biosensor Based on Aptamer-Modified Carbon Nanotube Field-Effect Transistors" Analytical Chemistry 79, 782-787, 2007.
(Continued)

*Primary Examiner* — Caitlyn Mingyun Sun
(74) *Attorney, Agent, or Firm* — Dierker & Kavanaugh, P.C.

(57) ABSTRACT

A sensing system includes a charge sensor including two electrodes and an electrically conductive channel connecting the two electrodes. The sensing system also includes a charged molecule attached to the electrically conductive channel. The charged molecule includes a recognition site to reversibly bind a label of a labeled nucleotide; has an unbound favored conformation associated with an unbound charge configuration; and has a favored conformation associated with a charge configuration when the recognition site is bound to the label. The charge configuration is different from the unbound charge configuration. The sensing system further includes a polymerase attached to the electrically conductive channel or to the charged molecule.

18 Claims, 6 Drawing Sheets

(51) Int. Cl.
*C12Q 1/68* (2018.01)
*G01N 33/543* (2006.01)

(56) References Cited

U.S. PATENT DOCUMENTS

| | | | |
|---|---|---|---|
| 2010/0111768 A1* | 5/2010 | Banerjee | G01N 21/6456 422/82.08 |
| 2011/0312529 A1* | 12/2011 | He | C12Q 1/6806 506/7 |
| 2012/0040865 A1 | 2/2012 | Kim | |
| 2013/0078622 A1 | 3/2013 | Collins et al. | |
| 2015/0065353 A1 | 3/2015 | Tumer et al. | |
| 2015/0068901 A1* | 3/2015 | Mannion | G01N 27/4145 204/601 |
| 2015/0316502 A1 | 11/2015 | Mohanty et al. | |
| 2016/0017416 A1* | 1/2016 | Boyanov | C12Q 1/6825 506/4 |
| 2017/0176429 A1* | 6/2017 | Samuels | C40B 40/00 |
| 2017/0219518 A1 | 8/2017 | Lee et al. | |
| 2018/0155773 A1 | 6/2018 | Gunderson et al. | |

FOREIGN PATENT DOCUMENTS

| | | |
|---|---|---|
| RU | 2199588 C2 | 2/2003 |
| RU | 2456618 C2 | 7/2012 |
| TW | 201502276 | 1/2015 |

OTHER PUBLICATIONS

Wu, et al., "Graphene Field-Effect Transistors for the Sensitive and Selective Detection of *Escherichia coli* Using Pyrene-Tagged DNA Aptamer" Advanced Healthcare Materials, Article No. 1700736, 1-9, 2017.

Kehagias, et al., "Stamp replication for thermal and UV nanoimprint lithography using a UV-sensitive silsesquioxane resist," Microelectronic Engineering 86, 776-778, 2009.

Nakatsuka, et al., "Aptamer-field-effect transistors overcome Debye length limitations for small-molecule sensing," Science, 10.1126/science.aao6750, Sep. 6, 2018.

* cited by examiner

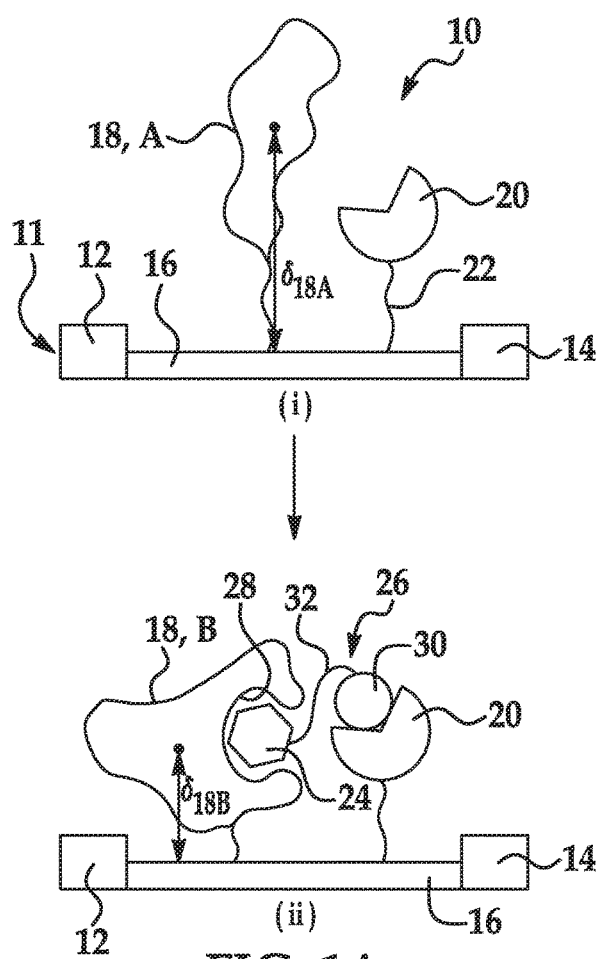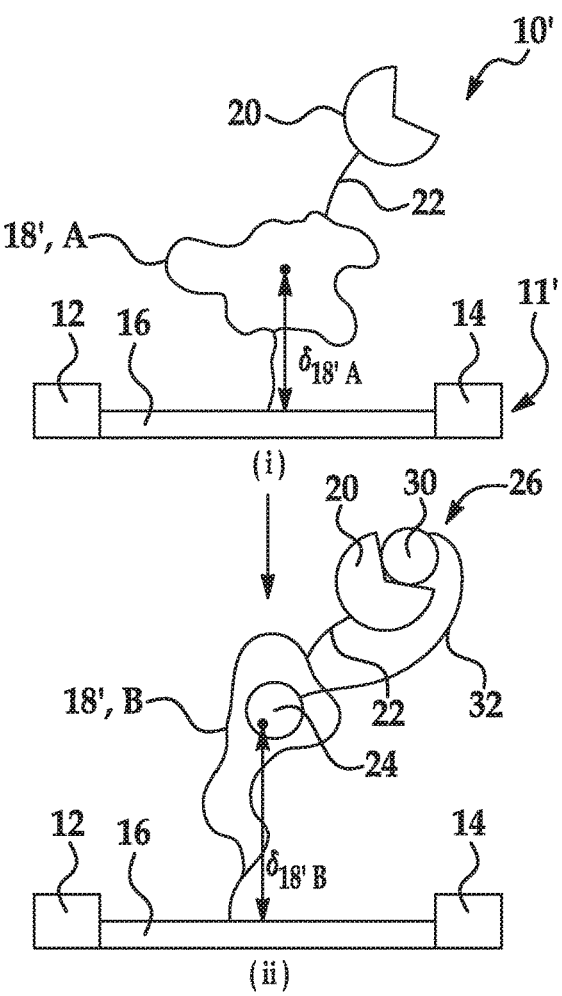
FIG. 1A  FIG. 1B
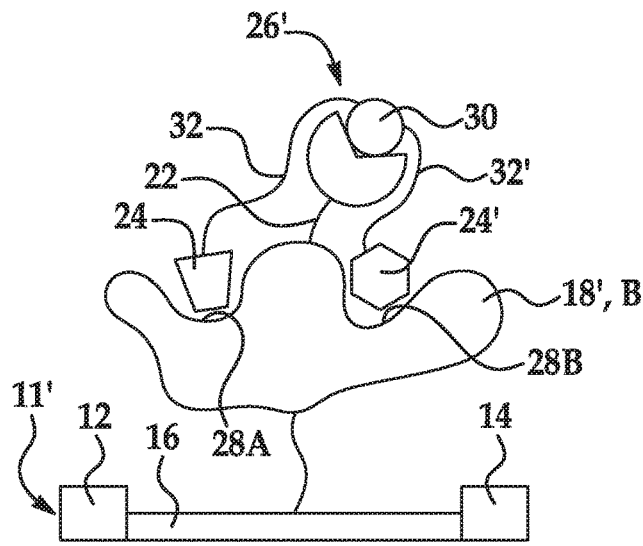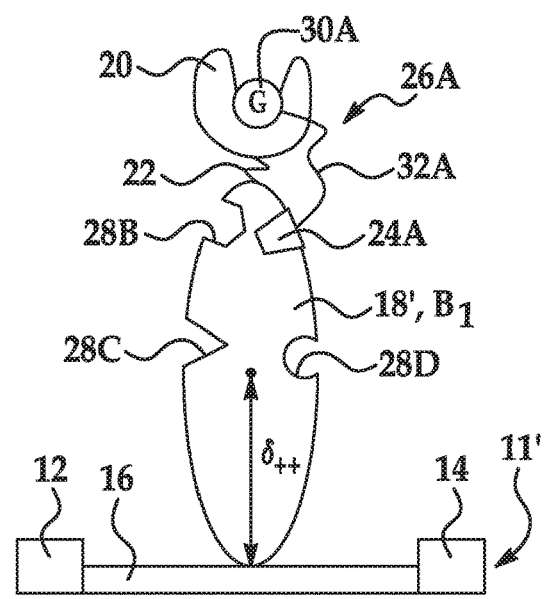
FIG. 2  FIG. 3A

SENSING SYSTEMS

CROSS-REFERENCE TO RELATED APPLICATION

This application claims the benefit of U.S. Provisional Application Ser. No. 62/783,951, filed Dec. 21, 2018; the content of which is incorporated by reference herein in its entirety.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. In some examples, the controlled reactions generate fluorescence, and thus an optical system may be used for detection. In other examples, the controlled reactions alter charge, conductivity, or some other electrical property, and thus an electronic system may be used for detection.

INTRODUCTION

A first aspect disclosed herein is a sensing system comprising a charge sensor including: two electrodes and an electrically conductive channel connecting the two electrodes; a charged molecule attached to the electrically conductive channel, wherein the charged molecule: includes a recognition site to reversibly bind a label of a labeled nucleotide, has an unbound favored conformation associated with an unbound charge configuration, and has a favored conformation associated with a charge configuration when the recognition site is bound to the label, wherein the charge configuration is different from the unbound charge configuration; and a polymerase attached to the electrically conductive channel or to the charged molecule.

In an example of this first aspect, the charged molecule is a charged aptamer. In this example, the charged aptamer is selected from the group consisting of a DNA aptamer, an RNA aptamer, and an analog thereof.

In an example of this first aspect, the charged molecule is selected from the group consisting of a charged protein and a charged peptide.

In an example of this first aspect, the charged molecule: further includes a second recognition site to reversibly bind a second label of a second labeled nucleotide and has a second favored conformation associated with a second charge configuration when the second recognition site is bound to the second label; further includes a third recognition site to reversibly bind a third label of a third labeled nucleotide and has a third favored conformation associated with a third charge configuration when the third recognition site is bound to the third label; and further includes a fourth recognition site to reversibly bind a fourth label of a fourth labeled nucleotide and has a fourth favored conformation associated with a fourth charge configuration when the fourth recognition site is bound to the fourth label; and the unbound favored conformation associated with the unbound charge configuration occurs when each of the recognition site, the second recognition site, the third recognition site, and the fourth recognition site is unbound.

In an example of this first aspect, the sensing system further comprises a second charged molecule attached to the electrically conductive channel, wherein the second charged molecule: includes a second recognition site to reversibly bind a second label of a second labeled nucleotide; has a second charged molecule unbound favored conformation associated with a second charged molecule unbound charge configuration; and has a second charged molecule favored conformation associated with a second charged molecule charge configuration when the second recognition site is bound to the second label. In this example, the sensing system may also further comprise a third charged molecule attached to the electrically conductive channel, wherein the third charged molecule: includes a third recognition site to reversibly bind a third label of a third labeled nucleotide; has a third charged molecule unbound favored conformation associated with a third charged molecule unbound charge configuration; and has a third charged molecule favored conformation associated with a third charged molecule charge configuration when the third recognition site is bound to the third label; and a fourth charged molecule attached to the electrically conductive channel, wherein the fourth charged molecule: includes a fourth recognition site to reversibly bind a fourth label of a fourth labeled nucleotide; has a fourth charged molecule unbound favored conformation associated with a fourth charged molecule unbound charge configuration; and has a fourth charged molecule favored conformation associated with a fourth charged molecule charge configuration when the fourth recognition site is bound to the fourth label.

In an example of this first aspect, the charged molecule further includes a second recognition site to reversibly bind a second label of a second labeled nucleotide and has a second favored conformation associated with a second charge configuration when the second recognition site is bound to the second label; and the sensing system further comprises a second charged molecule attached to the electrically conductive channel, wherein the second charged molecule: includes a third recognition site to reversibly bind a third label of a third labeled nucleotide, and a fourth recognition site to reversibly bind a fourth label of a fourth labeled nucleotide; has a second charged molecule unbound favored conformation associated with a second charged molecule unbound charge configuration; has a third favored conformation associated with a third charge configuration when the third recognition site is bound to the third label; and has a fourth favored conformation associated with a fourth charge configuration when the fourth recognition site is bound to the fourth label.

In an example of this first aspect, the charged molecule further includes a second recognition site to reversibly bind a second label of the labeled nucleotide.

It is to be understood that any features of the sensing system disclosed herein may be combined together in any desirable manner and/or configuration.

A second aspect disclosed herein is a sensing apparatus comprising a flow cell, and a sensing system integrated into the flow cell, the sensing system including a charge sensor including an electrically conductive channel; a charged molecule attached to the electrically conductive channel, wherein the charged molecule: has an unbound favored conformation associated with an unbound charge configuration; and has a favored conformation associated with a charge configuration when a recognition site of the charged molecule is bound to a label of a labeled nucleotide, wherein the charge configuration is different from the unbound charge configuration; and a polymerase attached to the electrically conductive channel or to the charged molecule.

In an example of this second aspect, the sensing apparatus further comprises a reagent delivery system to selectively introduce a reagent to an input of the flow cell. In some examples, the reagent is in a sample container, the reagent including the labeled nucleotide, which includes: a nucleotide; a linking molecule attached to a phosphate group of the nucleotide; and a recognition site specific label attached to the linking molecule.

In an example of this second aspect, the sensing apparatus further comprises a detector to detect a response from the charge sensor.

It is to be understood that any features of the sensing apparatus may be combined together in any desirable manner. Moreover, it is to be understood that any combination of features of the sensing system and/or of the sensing apparatus may be used together, and/or combined with any of the examples disclosed herein.

A third aspect disclosed herein is a method comprising introducing a template polynucleotide chain to a sensing system including: a charge sensor including two electrodes and an electrically conductive channel connecting the two electrodes; a charged molecule attached to the electrically conductive channel, wherein the charged molecule includes a recognition site; and a polymerase attached to the electrically conductive channel or to the charged molecule; introducing reagents including labeled nucleotides to the sensing system, whereby a nucleotide of one of the labeled nucleotides associates with the polymerase and a recognition site specific label of the one of the labeled nucleotides associates with the recognition site to induce a conformational change of the charged molecule; and in response to the conformational change of the charged molecule, detecting a response of the charge sensor.

In an example of this third aspect, the method further comprises associating the response of the charge sensor with the associated recognition site specific label; and based on the associated recognition site specific label, identifying the nucleotide of the one of the labeled nucleotides.

In an example of this third aspect, the charged molecule includes a plurality of different recognition sites, each of which is to reversibly bind a different label of a different labeled nucleotide at a distinct rate. In some examples, the method further comprises detecting a plurality of responses of the charge sensor in response to different conformational changes of the charged molecule when different labeled nucleotides respectively associate with the polymerase and different recognition site specific labels of the different labeled nucleotides respectively bind to one of the plurality of different recognition sites; and identifying the respectively associated different labeled nucleotides by the distinct rates.

In an example of this third aspect, the recognition site is to reversibly bind a plurality of different labels of a plurality of different labeled nucleotides at a plurality of distinct rates, and wherein the method further comprises: detecting a plurality of responses of the charge sensor in response to different conformational changes of the charged molecule when at least some of the different labeled nucleotides respectively associate with the polymerase and at least some of the different labels respectively bind to the recognition site; and identifying the respectively associated different labeled nucleotides by the distinct rates.

In an example of this third aspect, the recognition site is to reversibly bind up to four different labeled nucleotides, and wherein the method further comprises: detecting up to four different responses of the charge sensor in response to different conformational changes of the charged molecule when the up to four different labeled nucleotides respectively associate with the polymerase and the recognition site, wherein each of the up to four different responses has a distinct magnitude; and identifying the respectively associated different labeled nucleotides by the distinct magnitudes.

It is to be understood that any features of the method may be combined together in any desirable manner. Moreover, it is to be understood that any combination of features of the method and/or of the sensing system and/or of the sensing apparatus may be used together, and/or combined with any of the examples disclosed herein.

A fourth aspect disclosed herein is a sensing system comprising a charge sensor including: two electrodes and an electrically conductive channel connecting the two electrodes; a charged molecule attached to the electrically conductive channel, wherein the charged molecule: includes a recognition site to reversibly bind a label of a labeled nucleotide; has an unbound favored conformation associated with an unbound charge configuration; and has a favored conformation associated with a charge configuration when the recognition site is bound to the label, wherein the charge configuration is different from the unbound charge configuration; and a polymerase attached to at least one of the two electrodes or to a substrate on which the charge sensor is positioned.

In one example of the fourth aspect, the substrate is a patterned substrate, wherein the charge sensor is positioned in a depression of the patterned substrate, and wherein the polymerase is attached to a surface of the depression.

It is to be understood that any features of this sensing system may be combined together in any desirable manner. Moreover, it is to be understood that any combination of features of this sensing system and/or of the method and/or of the other sensing system and/or of the sensing apparatus may be used together, and/or combined with any of the examples disclosed herein.

A fifth aspect disclosed herein is a sensing apparatus, comprising a flow cell; and a sensing system integrated into the flow cell, the sensing system including: a charge sensor including an electrically conductive channel; a charged molecule attached to the electrically conductive channel, wherein the charged molecule: has an unbound favored conformation associated with an unbound charge configuration; and has a favored conformation associated with a charge configuration when a recognition site of the charged molecule is bound to a label of a labeled nucleotide, wherein the charge configuration is different from the unbound charge configuration; and a polymerase attached to at least one of the two electrodes or a substrate of the flow cell.

In one example of the fifth aspect, the substrate is a patterned substrate, wherein the charge sensor is positioned in a depression of the patterned substrate, and wherein the polymerase is attached to a surface of the depression.

It is to be understood that any features of this sensing apparatus may be combined together in any desirable manner. Moreover, it is to be understood that any combination of features of this sensing apparatus and/or of the method and/or sensing systems and/or of the other sensing apparatus may be used together, and/or combined with any of the examples disclosed herein.

Still further, it is to be understood that any features of any of the methods and/or of any of the sensing systems and/or any of the sensing apparatuses may be combined together in any desirable manner, and/or may be combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 1A is a schematic diagram of an example of a sensor disclosed herein, both when the charged molecule is in its unbound favored conformation (shown at "(i)") and its favored conformation (shown at "(ii)");

FIG. 1B is a schematic diagram of another example of a sensor disclosed herein, both when the charged molecule is in its unbound favored conformation (shown at "(i)") and its favored conformation (shown at "(ii)");

FIG. 2 is a schematic diagram of another example of a sensor disclosed herein;

FIGS. 3A through 3E are schematic diagrams illustrating another example of a sensor that includes a charged molecule having four different recognition sites;

DETAILED DESCRIPTION

Figure 3B:
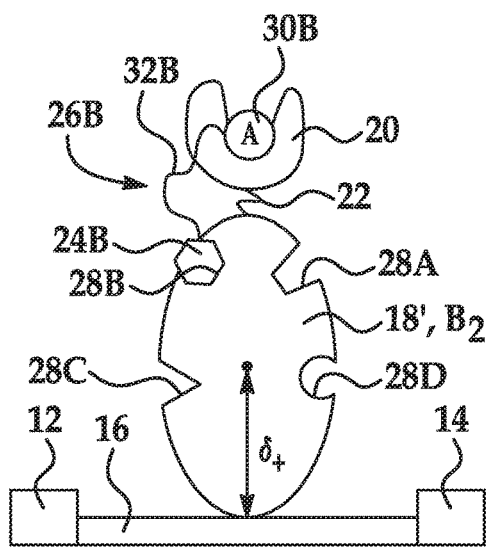

A sensing system is disclosed herein which may be used for single molecule detection in nucleic acid sequencing procedures. The sensing system includes a charged moiety attached to an electrically conductive channel of a charge sensor. The charged moiety is attached to the electrically conductive channel in such a manner that it is not detected until an event occurs (e.g., binding of a target label) that reconfigures the charged moiety to be detectable by the charge sensor. More specifically, the charged moiety is capable of undergoing reversible binding with a target label that is attached to a nucleotide that is capable of being incorporated by a polymerase. As a result of the target label binding to the charge moiety, the bound charged moiety undergoes a conformation change that alters the spatial distribution of the charges. Due to the proximity of the charged moiety with respect to the electrically conductive channel in the charge sensor, the charge sensor responds to the newly presented charges and produces a detectable signal. The detectable signal is produced even at biologically relevant or physiological concentrations of salt ions, where the Debye screening lengths are typically less than 1 nm. As examples, a conformation that moves a negatively charged moiety closer to the electrically conductive channel can decrease transconductance, while a conformation that moves the negatively charged moiety away from the electrically conductive channel can increase transconductance. As such, the different charged moiety conformations result in distinct detectable signals. Because the detectable charges reside on the charged moiety, charges do not need to reside on the target label, which can be advantageous.

In the examples disclosed herein, a target label can be customized to a particular nucleotide that is capable of being incorporated by a polymerase. Because the target label induces a desired conformational change in the charged moiety, the resulting signal can be used to identify a particular nucleotide. Moreover, in addition to charge magnitude, the on- and off-rates between target labels and one or more charged moieties may be used to generate unique fingerprint signals that manifest with unique frequencies, which can be used to identify respective nucleotides linked to the target labels.

Referring now to FIGS. 1A and 1B, two examples of the sensing system 10, 10' are respectively depicted. Each of the sensing systems 10, 10' includes a charge sensor 11, 11', which includes two electrodes 12, 14 and an electrically conductive channel 16 connecting the two electrodes 12, 14. The sensing systems 10, 10' also include a charged molecule 18 or 18' attached to the electrically conductive channel 16 of the charge sensor 11, 11', and a polymerase 20 attached to the electrically conductive channel 16 (FIG. 1A) or to the charged molecule 18' (FIG. 1B).

In other examples of the sensing system, the polymerase 20 may be attached to other components of the sensing system 10, 10' (e.g., to an electrode 12 or 14) and/or to other components of a flow cell in which the sensing system 10, 10' is integrated. The polymerase 20 may be attached to any area adjacent to the charge sensor 11, 11' as long as a label of a nucleotide being incorporated by the polymerase 20 can be reversibly bound to the charged molecule 18 or 18'. In some examples, the polymerase 20 is attached within a distance of about 5 nm to about 50 nm of the charged molecule 18 or 18'.

The charge sensor 11, 11' may be a field effect transistor (FET), such as a carbon nanotube (CNT) based FET, single-walled carbon nanotube (SWNT) based FET, silicon nanowire (SiNW) FET, silicon nanotube FET, a polymer nanowire FET, a graphene nanoribbon FET (and related nanoribbon FETs fabricated from 2D materials such as $MoS_2$, silicene, etc.), a metal-oxide semiconductor FET (MOSFET), a tunnel FET (TFET), or any other device with conductance that can be modulated by an external field, for example a metallic CNT or a multi-walled CNT. In the FET, the electrodes 12, 14 are the source and drain terminals and the electrically conductive channel 16 is the gate terminal. The field effect transistor may be a PMOS, or p-channel, having p-type source and drain terminals in an n-type substrate, or an NMOS, or n-channel, having n-type source and drain terminals in a p-type substrate.

The electrodes 12, 14 may comprise any suitable conductive material. Examples of suitable source and drain materials include cobalt, cobalt silicide, nickel, nickel silicide, aluminum, tungsten, copper, titanium, molybdenum, indium tin oxide (ITO), indium zin oxide, gold, platinum, carbon, etc.

The electrically conductive channel 16 may be a nanostructure that has at least one dimension on the nanoscale (ranging from 1 nm to less than 1 μm). In one example, the at least one dimension refers to the largest dimension.

The electrically conductive channel 16 may also have any suitable geometry, such as a tubular structure, a wire structure, a planar structure, etc., and may be any suitable semi-conductive or conductive material. As examples, the electrically conductive channel 16 may be selected from the group consisting of a semi-conducting nanostructure, a graphene nanostructure, a metallic nanostructure, a conducting polymer nanostructure, or a molecular wire. In some examples, the nanostructure may be a multi- or single-walled nanotube, a nanowire, a nanoribbon, etc. As specific examples, the nanostructure may be a carbon nanotube, a single-walled carbon nanotube, a silicon nanowire, a silicon nanotube, a polymer nanowire, a graphene nanoribbon, a MoS$_2$ nanoribbon, a silicon nanoribbon, etc.

In the system 10, 10', the charged molecule 18, 18' is attached, either covalently or non-covalently, to the electrically conductive channel 16 of the charge sensor 11, 11'. The charged molecule 18, 18' may be directly bonded to the electrically connective channel 16, or may be indirectly bonded to the electrically conductive channel 16 through a tether. The attachment of the charged molecule 18, 18' maintains the charged molecule 18, 18' within the vicinity, e.g., within a few Debye lengths, of the electrically conductive channel 16. Any suitable charged molecule 18, 18' may be used that can undergo reversible binding with a target label 24 of a labeled nucleotide 26. More particularly, the charged molecule 18, 18' includes a recognition site 28 that is capable of reversibly binding to the label 24, has an unbound favored conformation A associated with an unbound charge configuration (see the top portion (labeled (i)) in each of FIG. 1A and FIG. 1B), and has a favored conformation B associated with a charge configuration when the recognition site 28 is bound to the label 24 (see the bottom portion (labeled (ii) in each of FIG. 1A and FIG. 1B)).

The term "unbound favored conformation" refers to one spatial arrangement that is preferentially exhibited by the charged molecule 18, 18' when the label 24 is not bound thereto. The charged molecule 18, 18' can dynamically move between several different conformations when the label 24 is not bound. However, the charged molecule 18, 18' has a preferred spatial arrangement that is exhibited more often than the other spatial arrangements when the target label 24 is not bound. In this example, this preferred spatial arrangement (or preferentially exhibited spatial arrangement) is the most probable arrangement, e.g., due to molecule stability and/or being its lowest energy state, and thus is the unbound favored conformation A. The unbound favored conformation A may, in some instances, be the most stable conformation and/or the lowest energy conformation.

The unbound favored conformation A is associated with an unbound charge configuration. The unbound charge configuration is the distribution of the charges of the charged molecule 18, 18' when it is in its unbound favored conformation A.

The term "favored conformation" refers to one spatial arrangement that is preferentially exhibited by the charged molecule 18, 18' when the label 24 is reversibly bound thereto. The favored conformation B of the charged molecule 18, 18' is different from the unbound favored conformation A. When the target molecule binds to the charged molecule 18, 18', the charged molecule 18, 18' moves to a preferred spatial arrangement that is exhibited more often than the other spatial arrangements when the target label is bound. In this example, this preferred spatial arrangement is the most probable arrangement, e.g., due to molecule stability, when the target label is bound, and thus is the favored conformation. In one example, the charged molecule 18, 18' has multiple conformations in equilibrium, and the label 24 is able to stabilize one of the conformations.

The favored conformation B is associated with a charge configuration. The charge configuration is the distribution of the charges of the charged molecule 18, 18' when it is in its favored conformation B. The charge configuration associated with the favored conformation B is detectably different from the unbound charge configuration. The charge configuration may be detectable (by the charge sensor) as an increased or decreased magnitude, or a change in frequency, etc.

As mentioned, the label 24 of the labeled nucleotide 26 is capable of reversibly binding to the recognition site 28. As such, the recognition site 28 is a temporary receptor for the label 24.

The top portions (labeled (i)) of FIG. 1A and FIG. 1B show the charged molecule 18, 18' in the unbound favored conformation A. As mentioned herein, the unbound favored conformation A refers to the preferred orientation or spatial arrangement of the charged molecule 18, 18' when the recognition site 28 does not have the label 24 bound thereto. The unbound conformation A (shown at (i) in FIG. 1A and FIG. 1B) is associated with an unbound charge configuration. The unbound charge configuration is the distribution of the charges of the charged molecule 18, 18' when it is in its unbound favored conformation A. In FIG. 1A and FIG. 1B, the centroid of the charge distribution is shown as "•" and the distance between the charge centroid and the surface of the electrically conductive channel 16 is shown as "$\delta_{18A}$" (FIG. 1A) and "$\delta_{18'A}$" (FIG. 1B). As illustrated in these figures, the charge distribution, the centroid, and the distance $\delta_{18A}$, $\delta_{18'A}$ are different for each charged molecule 18, 18', and can be altered when the charged molecule 18, 18' binds to the target label 24.

The bottom portions (labeled (ii)) of FIG. 1A and FIG. 1B show the charged molecule 18, 18' in the favored conformation B, i.e., when the target label 24 is bound to the recognition site 28. As mentioned herein, the favored conformation B (shown at (ii) in FIG. 1A and FIG. 1B) refers to the preferred orientation or spatial arrangement of the charged molecule 18, 18' when the label 24 is bound to the recognition site 28. The favored conformation B is associated with a charge configuration. The charge configuration is the distribution of the charges of the charged molecule 18, 18' when it is in its favored conformation B. In FIG. 1A(ii), the favored conformation B of the charged molecule 18 moves the charged molecule 18 closer to the surface of the electrically conductive channel 16 when compared to the unbound favored conformation A. In this example of the favored conformation B, $\delta_{18B}$ is less than $\delta_{18A}$ and the negative or positive charges of the charged molecule 18 are closer in proximity to the electrically conductive channel 16. In FIG. 1B(ii), the favored conformation B of the charged molecule 18' moves the charged molecule 18' away from the surface of the electrically conductive channel 16 when compared to the unbound favored conformation A. In this example of the favored conformation B, $\delta_{18'B}$ is greater than $\delta_{18'A}$ and the negative or positive charges of the charged molecule 18 are further away from the electrically conductive channel 16. The conductivity of the electrically conductive channel 16 changes in response to the motion of the charge of the charged molecule 18, 18'. In the examples disclosed herein, the sign of the change in the two directions of motion are opposite to one another; and the actual sign depends on the nature of the sensing system 10, 10'. As examples, the sign of the response and repulsion or retraction depend on whether the charge sensor 11, 11' is a FET, and if it is a FET, whether the FET is in depletion or inversion mode, and if the channel carriers are electrons and holes.

The charged molecule 18, 18' may be a charged aptamer, a charged protein, or a charged peptide. As used herein, the term "charged aptamer" refers to a structured and charged nucleic acid capable of: 1) reversibly binding to a label, and 2) changing its favored conformation, and thereby the distribution of charges, upon reversibly binding to the label; the term "charged protein" refers to a structured and charged macromolecule capable of: 1) reversibly binding to a label, and 2) changing its favored conformation, and thereby the distribution of charges, upon reversibly binding to the label; and the term "charged peptide" refers to a structured and charged short chain of amino acid monomers linked by peptide (amide) bonds: 1) reversibly binding to a label, and 2) changing its favored conformation, and thereby the distribution of charges, upon reversibly binding to the label.

In some examples, the charged molecule 18, 18' is negatively charged. Examples of suitable negatively charged molecules 18, 18' include negatively charged aptamers, negatively charged proteins, negatively charged peptides, and other negatively charged molecules. Some specific examples of negatively charged aptamers include DNA aptamers, RNA aptamers, or analogs thereof. Some specific examples of negatively charged proteins include HSF1 (−17), SHFM1 (−21), NFKBIA (−25), RBBP4 (−26), APP (−55), PJA2 (−87), and many others. Examples of negatively charged peptides include polyglutamate and polyaspartate, as well as more structured peptides, such as coiled coils with negatively charged surfaces.

In some examples, the charged molecule is positively charged. Examples of suitable positively charged molecules 18, 18' include positively charged aptamers, positively charged proteins, positively charged peptides, and other positively charged molecules. Some specific examples of positively charged proteins include H2AFX (+17), PARP1 (+21), ELN (+40), TERT (+98), and many others. Examples of positively charged peptides include polylysine and polyarginine, as well as more structured peptides, such as coiled coils with positively charged surfaces.

In an example, the charged molecule 18, 18' is not a polymerase.

The charged molecule 18, 18' may be attached to the electrically conductive channel 16 of the charge sensor 11, 11' directly or indirectly and/or through covalent bonding or non-covalent bonding. The type of bond formed between the charged molecule 18, 18' and the electrically conductive channel 16 will depend upon the molecule 18, 18' and channel 16 used. When an aptamer is used as the charged molecule 18, 18', the electrically conducting channel 16 may be silanized to generate amine terminated silanes, which can bind with thiolated aptamers. Other examples of suitable surface chemistry that may be used to bind the charged molecule 18, 18' may include (1-ethyl-3-(3-dimethylaminopropyl)carbodiimide hydrochloride) (EDC), diarylcyclooctyne (DBCO), azides that can undergo copper catalyzed click reaction, etc. In other examples, a tether may be used to attach the charged molecule 18, 18' to the electrically conducting channel 16. This tether may be any of the examples described herein for tether 22.

In the example shown in FIG. 1A, the polymerase 20 is immobilized on the electrically conductive channel 16 of the charge sensor 11, 11'. In the example shown in FIG. 1B, the polymerase 20 is immobilized on the charged molecule 18'. In other examples, the polymerase 20 is immobilized on one of the electrodes 12 or 14 (see FIG. 7B). In still other examples, the polymerase 20 is immobilized on a substrate, e.g., which supports the charge sensor 11, 11' (see FIG. 7B). In any instance, the polymerase 20 may be immobilized via a tether 22. The tether 22 is used as an anchor for the polymerase 20. An example of a suitable tether 22 includes polyethylene glycol (PEG). In some examples, the tether 22 holds the polymerase 20 at least 10 nm away from the electrically conductive channel 16 or from the charged molecule 18. This may be desirable, for example, so that conformal changes to the polymerase 20, charges of the polymerase 20, and/or charges of the target/template polynucleotide chain held by the polymerase 20 do not interfere with the sensing operation of the charge sensor 11, 11'.

Any suitable polymerase 20 may be used. Examples include polymerases from family A, such as Bsu Polymerase, Bst Polymerase, Taq Polymerase, T7 Polymerase, and many others; polymerases from family B, such as Phi29 polymerase, Pfu Polymerase, KOD Polymerase, and many others; polymerases from family C, such as *Escherichia coli* DNA Pol III, and many others, polymerases from family D, such as *Pyrococcus furiosus* DNA Pol II, and many others; polymerases from family X, such as DNA Pol μ, DNA Pol β, DNA Pol σ, and many others.

It is to be understood that the polymerase 20 is not released as a result of the target label 24 binding to the charged molecule 18, 18'. Rather, the polymerase 20 remains tethered, e.g., to the channel 16 or to the charged molecule 18, 18' or to some other flow cell component, as the binding event takes place and after the binding event takes place.

In some examples disclosed herein, the charged molecule 18, 18' and the polymerase 20 are different (separate and distinct) entities having different roles/functions, which together enable single molecule sensing. In an example of single molecule sensing, a signal is detected at the charge sensor 11, 11' as a nucleotide is incorporated into a nascent strand that is formed along a template chain. During one example nucleotide incorporation event, the polymerase 20 holds a template polynucleotide chain and incorporates one nucleotide into the nascent strand that is complementary to a nucleotide along the template, while the charged molecule 18, 18' reversibly binds a label (that is attached to the nucleotide that is being incorporated) and undergoes a conformational change that results in an identifiable signal at the charge sensor 11, 11'. As mentioned herein, in some examples, it may be desirable to configure the polymerase 20 (e.g., by adjusting the length of the tether 22) so that any conformational changes of the polymerase 20 do not interfere with the signal generated by the conformational change of the charged molecule 18, 18'.

As shown in FIGS. 1A(ii) and 1B(ii), the labeled nucleotide 26 is introduced to the sensing system 10, 10'. The labeled nucleotide 26 includes a nucleotide 30, a linking molecule 32 attached to a phosphate group of the nucleotide 30, and a recognition site specific label 24 (also referred to as the label 24 or the target label 24) attached to the linking molecule 32. The labeled nucleotide 26 may be considered a non-natural or synthetic nucleotide because it is structurally or chemically distinct from a natural nucleotide.

Figure 5:
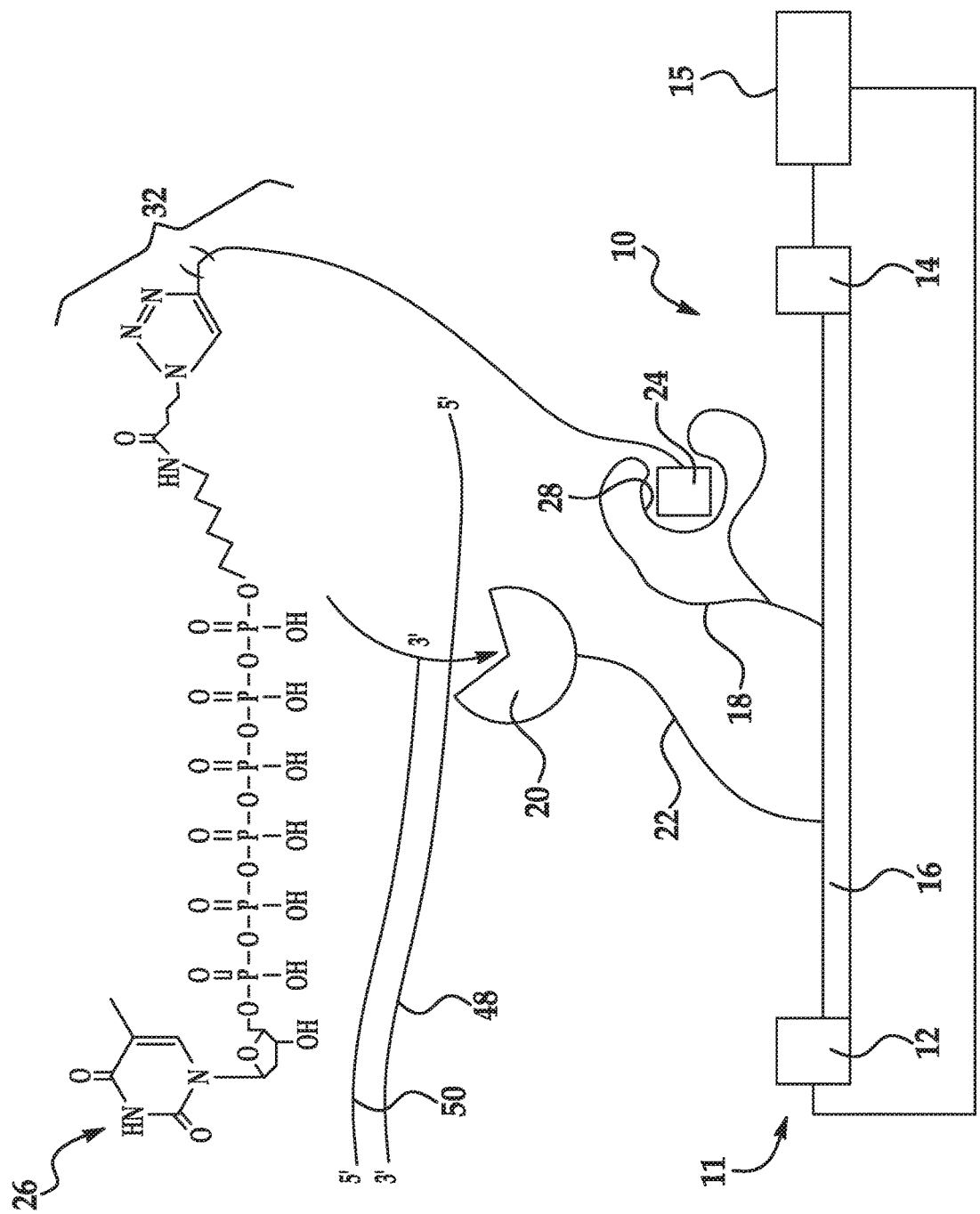
FIG. 5 schematically illustrates an example of a method disclosed herein.

The nucleotide 30 of the labeled nucleotide 26 may be a natural nucleotide. Natural nucleotides include a nitrogen-containing heterocyclic base, a sugar, and one or more phosphate groups. Examples of natural nucleotides include, for example, ribonucleotides or deoxyribonucleotides. In a ribonucleotide, the sugar is a ribose, and in a deoxyribonucleotide, the sugar is a deoxyribose (i.e., a sugar lacking a hydroxyl group that is present at the 2' position in ribose). In an example, the nucleotide 30 is in the polyphosphate form because it includes several phosphate groups (e.g., tri-phosphate (i.e., gamma phosphate), tetra-phosphate, penta-phosphate, hexa-phosphate (as shown in FIG. 5), etc.). The heterocyclic base (i.e., nucleobase) can be a purine base or a pyrimidine base or any other nucleobase analog. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

The labeled nucleotide 26 also includes the linking molecule 32. The linking molecule 32 may be any long chain molecule that can chemically bond, at one end, to the phosphate group(s) of the nucleotide 30 and that can chemically bond, at the other end, to the label 24. The linking molecule 32 may also be selected so that it will not interact with the polymerase 20. The linking molecule 32 is selected so that it is long enough to permit the label 24 to associate with the recognition site 28 of the charged molecule 18, 18' while, for example, the nucleotide 30 is held by the polymerase 20.

As examples, the linking molecule 32 may include an alkyl chain, a poly(ethylene glycol) chain, an amido group, a phosphate group, a heterocycle such as a triazole, nucleotides, or combinations thereof. Examples of the alkyl chain may include at least 6 carbon atoms and examples of the poly(ethylene glycol) chain may include at least 3 ethylene glycol units.

The following example illustrates an example of the labeled nucleotide 26, where the linking molecule 32 comprises an alkyl chain, an amide group, a poly(ethylene glycol) chain, and a triazole:

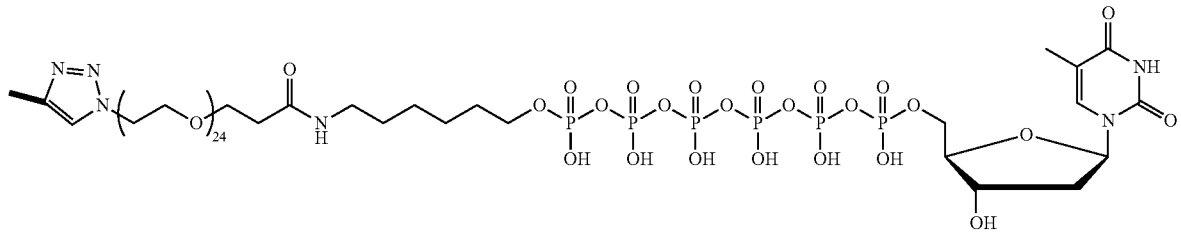

Recognition site specific label

The following example illustrates another example of the labeled nucleotide 26, where the linking molecule 32 comprises alkyl chains, an amide group, poly(ethylene glycol) chains, a triazole, and a phosphate group:

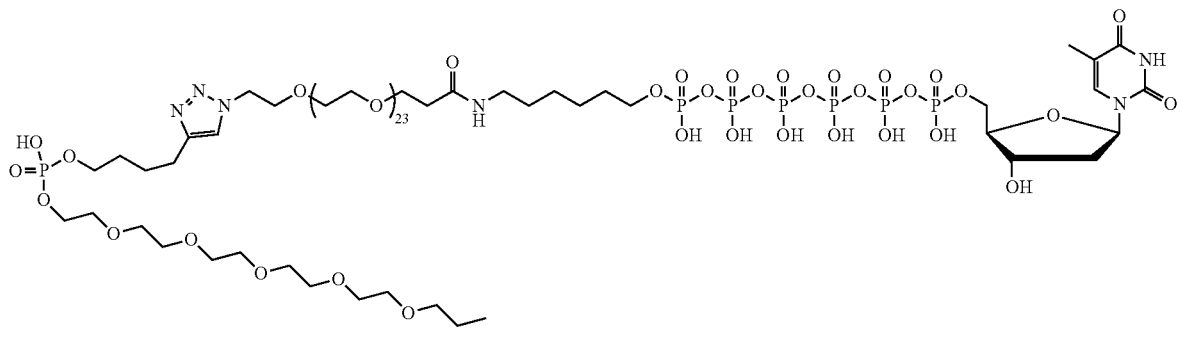

Recognition site specific label

The following example illustrates yet another example of the labeled nucleotide 26, where the linking molecule 32 comprises alkyl chains, amide groups, poly(ethylene glycol) chains, a triazole, and a phosphate group:

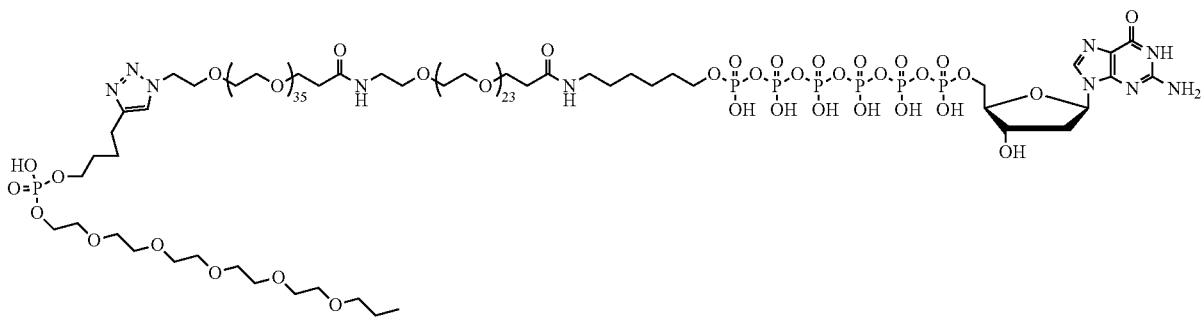

Recognition site specific label

The following example illustrates still a further example of the labeled nucleotide 26, where the linking molecule 32 comprises an alkyl chains, an amide group, poly(ethylene glycol) chains, a triazole, a phosphate group and a polynucleotide chain:

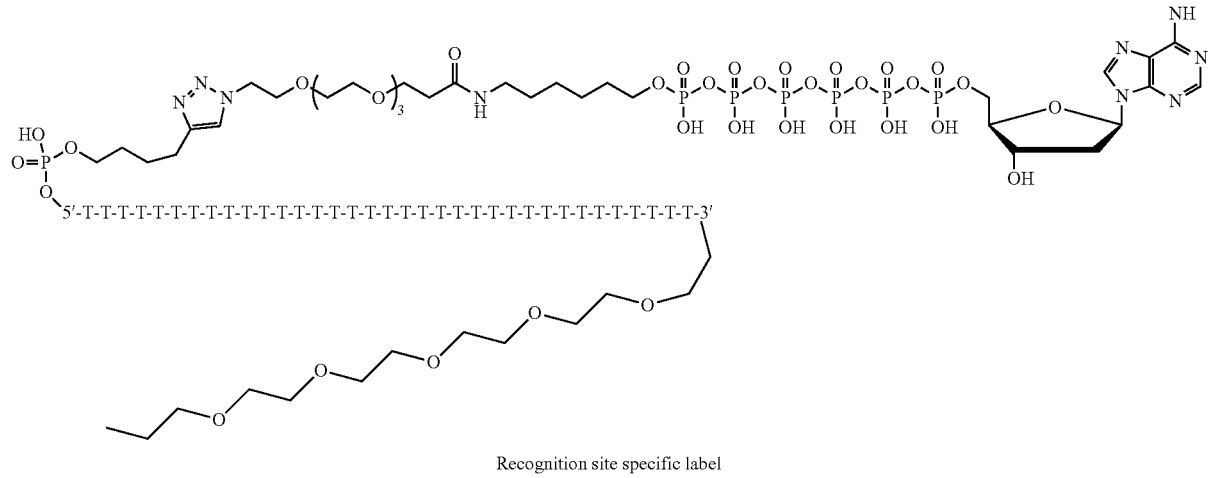

Recognition site specific label

While several example linking molecules 32 have been described, it is to be understood that other linking molecules 32 may be used.

The recognition site specific label 24 is a molecule that can be recognized by the charged molecule 18, 18', and that can reversibly bind to the charged molecule 18, 18' at the recognition site 28. Examples of suitable recognition site specific labels 24 include antibiotics, such as Kanamycin, Lividomycin, Tobramycin, Neomycin, Viomycin, Streptomycin, and others; enzyme cofactors, such as FMN, NAD, Vitamin B12, Xanthene, and others; amino acids, such as arginine, citrulin, argininamide, valine, isoleucine, tryptophan, and others; and many miscellaneous small molecules, such as theophylline, dopamine, sulforhodamine, cellobiose, and others.

FIG. 1A and FIG. 1B illustrate examples of a charged molecule 18, 18' that is capable of binding to one target label 24 of one labeled nucleotide 26. In other examples, one labeled nucleotide 26 may include multiple labels 24 that can bind to a single charged molecule 18, 18' (FIG. 2), or one charged molecule 18, 18' may include multiple recognition sites 28, each of which can bind to a respective label 24 of a respective nucleotide (FIG. 3A through FIG. 3E).

In FIG. 2, the charged molecule 18' includes a first recognition site 28A that is to reversibly attach a first label 24 of the labeled nucleotide 26', and further includes a second recognition site 28B that is to reversibly attach a second label 24' of the labeled nucleotide 26'. This example includes three different conformational changes—one when the first label 24 alone is bound, another when the second label 24' alone is bound, and still another when both of the labels 24, 24' are bound simultaneously. In FIG. 2, the specific conformational change of the charged molecule 18' is achieved by binding the two different labels 24, 24' to the two different recognition sites 28A, 28B. As illustrated, the one labeled nucleotide 26' includes both of the labels 24 and 24', and these labels 24, 24' are attached to one nucleotide 30 by respective linking molecules 32 and 32'. Any examples of the labels 24 and linking molecules 32 may be used in this example of the labeled nucleotide 26', as long as the labels 24 and 24' are different from each other and can be recognized by the recognition sites 28A and 28B of the charged molecule 18' either separately or at the same time. In the example shown, when both of the labels 24, 24' are bound, the charged molecule 18' is in one of its modified conformations B and a detectable signal results.

While the charged molecule 18' with the polymerase 20 attached thereto is shown in FIG. 2, it is to be understood that the charged molecule 18 and separately attached polymerase 20 may be used in the example shown in FIG. 2.

In still another example not shown in the drawings, the charged molecule 18, 18' includes two recognition sites (e.g., 28A, 28B), either of which can bind to a single label 24 that is attached to the nucleotide 30. This example includes two different favored conformational changes—one when the label 24 binds to the first recognition site 28A and another when the label 24 binds to the second recognition site 28B.

In FIG. 3A through FIG. 3E, the charged molecule 18' includes four different recognition sites 28A, 28B, 28C, 28D, each of which is capable of reversibly binding to a different target label 24A, 24B, 24C, 24D of different labeled nucleotides 26A, 26B, 26C, 26D. While the charged molecule 18' with the polymerase 20 attached thereto is shown in FIG. 3A through FIG. 3E, it is to be understood that the charged molecule 18 and separately attached polymerase 20 may be used in the example shown in FIG. 3A through FIG. 3E.

Figure 3C:
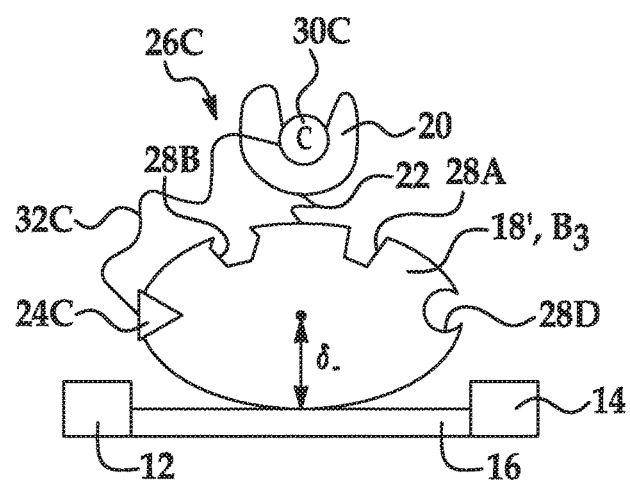
Figure 3D:
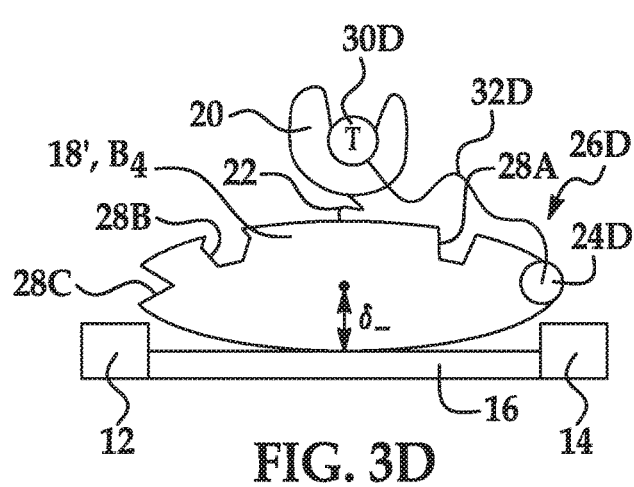

In this example, as shown in FIG. 3A, the charged molecule 18' includes a first recognition site 28A to reversibly attach a first label 24A of a first labeled nucleotide 26A, and has a first favored conformation $B_1$ associated with a first charge configuration when the first recognition site 28A is bound to the first label 24A. As shown in FIG. 3B, the charged molecule 18' further includes a second recognition site 28B to reversibly attach a second label 24B of a second labeled nucleotide 26B, and has a second favored conformation $B_2$ associated with a second charge configuration when the second recognition site 28B is bound to the second label 24B. As shown in FIG. 3C, the charged molecule 18' further includes a third recognition site 28C to reversibly attach a third label 24C of a third labeled nucleotide 26C, and has a third favored conformation $B_3$ associated with a third charge configuration when the third recognition site 28C is bound to the third label 24C. As shown in FIG. 3D, the charged molecule 18' further includes a fourth recognition site 28D to reversibly attach a fourth label 24D of a fourth labeled nucleotide 26D, and has a fourth favored conformation $B_4$ associated with a fourth charge configuration when the fourth recognition site 28D is bound to the fourth label 24D.

Figure 3E:
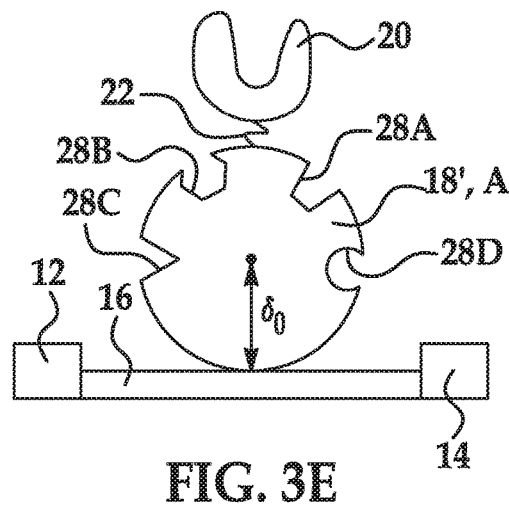

The unbound favored conformation A of the charged molecule 18' is shown in FIG. 3E. As depicted, the unbound favored conformation A of this example (which is associated with the unbound charge configuration) occurs when each of the first recognition site 28A, the second recognition site 28B, the third recognition site 28C, and the fourth recognition site 28C is unbound (i.e., no labeled nucleotides 26A-26D are bound to the sites 28A-28D). The centroid of the charge distribution for the unbound favored conformation A has a set distance $\delta_0$ from the surface of the electrically conductive channel 16. This distance $\delta_0$ is altered depending upon the labeled nucleotide 26A-26D that is reversibly bound to the charged molecule 18'.

In the example shown in FIG. 3A, the labeled nucleotide 26A includes guanine polyphosphate as the nucleotide 30A, a linker 32A, and a unique label 24A. When the polymerase 20 incorporates the nucleotide 30A, the effective concentration of the label 24A is effectively increased within proximity of the charged molecule 18' (which has a recognition site 24A for the label 24A), causing the charged molecule 18' to bind the label 24A. In the example shown in FIG. 3A, the binding causes the distance $\delta_0$ between the charge centroid and the channel surface to increase, as denoted by "$\delta_{++}$".

In the example shown in FIG. 3B, the labeled nucleotide 26B includes adenine polyphosphate as the nucleotide 30B, a linker 32B, and a unique label 24B. When the polymerase 20 incorporates the nucleotide 30B, the effective concentration of the label 24B is effectively increased within proximity of the charged molecule 18' (which has a recognition site 24B for the label 24A), causing the charged molecule 18' to bind the label 24B. In the example shown in FIG. 3B, the binding causes the distance $\delta_0$ between the charge centroid and the channel surface to increase, as denoted by "$\delta_+$". While the favored conformational changes shown in FIG. 3A and FIG. 3B both result in increased distances $\delta_{++}$ and $\delta_+$, the distances $\delta_{++}$ and $\delta_+$ are different and thus will result in distinct measurable signals.

In the example shown in FIG. 3C, the labeled nucleotide 26C includes cytosine polyphosphate as the nucleotide 30C, a linker 32C, and a unique label 24C. When the polymerase 20 incorporates the nucleotide 30C, the effective concentration of the label 24C is effectively increased within proximity of the charged molecule 18' (which has a recognition site 24C for the label 24C), causing the charged molecule 18' to bind the label 24C. In the example shown in FIG. 3C, the binding causes the distance $\delta_0$ between the charge centroid and the channel surface to decrease, as denoted by "$\delta_-$".

In the example shown in FIG. 3D, the labeled nucleotide 26D includes thymine polyphosphate as the nucleotide 30D, a linker 32D, and a unique label 24D. When the polymerase 20 incorporates the nucleotide 30D, the effective concentration of the label 24D is effectively increased within proximity of the charged molecule 18' (which has a recognition site 24D for the label 24D), causing the charged molecule 18' to bind the label 24D. In the example shown in FIG. 3D, the binding causes the distance $\delta_0$ between the charge centroid and the channel surface to decrease, as denoted by "$\delta_-$". While the favored conformational changes shown in FIG. 3C and FIG. 3D both result in decreased distances $\delta_-$ and $\delta_{--}$, the distances $\delta_-$ and $\delta_{--}$ are different and thus will result in distinct measurable signals.

In the example shown in FIG. 3A through FIG. 3E, one charged molecule 18' has four different recognition sites 28A-28D and thus has four different modified configurations that result in four different and distinct measurable signals. These different and distinct signals enable four different nucleotides 30A-30D to be identified as they are respectively incorporated into a template strand.

Other variations of the multi-recognition site charged molecule are also contemplated. For example, two charged molecules 18, 18', each having two different recognition sites 28, could be attached to the electrically conductive channel 16 of the charge sensor 11, 11'. For each of these charged molecules 18, 18', the unbound favored conformation A would be exhibited when the two different recognition sites remain unbound. In this example, a first of the two charged molecules 18, 18' includes a first recognition site (e.g., 28A in FIG. 3A) to reversibly attach a first label (e.g., 24A in FIG. 3A) of a first labeled nucleotide (e.g., 26A in FIG. 3A) and has a first favored conformation (e.g., $B_1$ in FIG. 3A) associated with a first charge configuration when the first recognition site is bound to the first label, and further includes a second recognition site (e.g., 28B in FIG. 3B) to reversibly attach a second label (e.g., 28B in FIG. 3A-FIG. 3E) of a second labeled nucleotide (e.g., 26B in FIG. 3A-FIG. 3E) and has a second favored conformation (e.g., $B_2$ in FIG. 3B) associated with a second charge configuration when the second recognition site is bound to the second label. In this example, the second of the two charged molecules 18, 18' includes a third recognition site (e.g., 28C in FIG. 3C) to reversibly attach a third label (e.g., 24C in FIG. 3C) of a third labeled nucleotide (e.g., 26C in FIG. 3C) and a fourth recognition site (e.g., 28D in FIG. 3D) to reversibly attach a fourth label (e.g., 24D in FIG. 3D) of a fourth labeled nucleotide (e.g., 26D in FIG. 3D), and also has a third favored conformation (e.g., $B_3$ in FIG. 3C) associated with a third charge configuration when the third recognition site is bound to the third label and has a fourth favored conformation (e.g., $B_4$ in FIG. 3D) associated with a fourth charge configuration when the fourth recognition site is bound to the fourth label. In this example, two different charged molecules 18, 18' may be used to identify four different labeled nucleotides 26A-26D.

In still other examples, the sensing system 10, 10' may include several charged molecules 18, 18' attached to the electrically conductive channel 16 of the charge sensor 11, 11'. In one example, each of the charged molecules 18, 18' is capable of reversibly binding to a different labeled nucleotide 26. An example of this sensing system 10" is shown in FIG. 4.

In this example, four different charged molecules 18A, 18B, 18C, 18D are attached to the electrically conductive channel 16 of the charge sensor 11". In this example, each of the charged molecules 18A, 18B, 18C, 18D has its own recognition site, unbound favored conformation, and favored conformation (during label binding) that is independent of each of the other charged molecules 18A, 18B, 18C, 18D. More specifically, a first charged molecule 18A attached to the electrically conductive channel 16 includes a first recognition site to reversibly bind a first label of a first labeled nucleotide, an unbound favored conformation when the first recognition site is unbound, and a favored conformation with a charge configuration when the first recognition site is bound to the first label. In this example, a second charged molecule 18B attached to the electrically conductive channel 16 includes a second recognition site to reversibly bind a second label of a second labeled nucleotide, a second charged molecule unbound favored conformation, and a second charged molecule favored conformation with a second charged molecule charge configuration when the second recognition site is bound to the second label. Also in this example, a third charged molecule 18C attached to the electrically conductive channel 16 includes a third recognition site to reversibly bind a third label of a third labeled nucleotide, a third charged molecule unbound favored conformation, and a third charged molecule favored conformation with a third charged molecule charge configuration when the third recognition site is bound to the third label. Also in this example, a fourth charged molecule 18D attached to the electrically conductive channel 16 includes a fourth recognition site to reversibly bind a fourth label of a fourth labeled nucleotide, a fourth charged molecule unbound favored conformation, and a fourth charged molecule favored conformation with a fourth charged molecule charge configuration when the fourth recognition site is bound to the fourth label.

Figure 4:
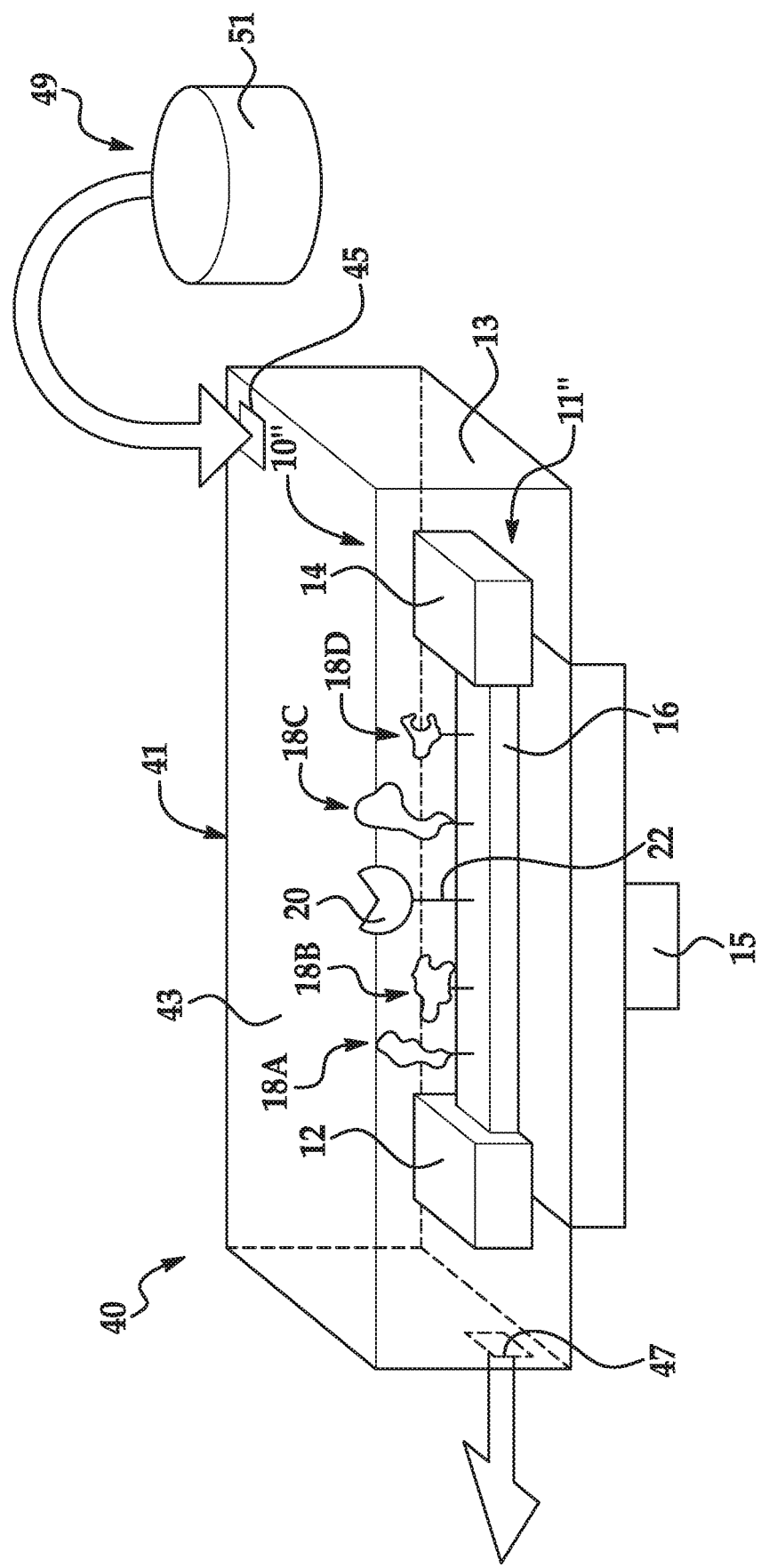
FIG. 4 is a schematic, perspective diagram of an example of a sensing system including a flow cell and an example of the sensor disclosed herein.

As shown in FIG. 4, a single polymerase 20 may be bound to the electrically conductive channel 16. In this example, the length of each linking molecule 32 of the respective labeled nucleotides 26 may be selected so that when a respective nucleotide 30 is held by the polymerase 20, the respective label 24 can bind with its corresponding charged molecule 18A, 18B, 18C, 18D, and not with an adjacent charged molecule 18A, 18B, 18C, 18D.

FIG. 4 also illustrates an example of the sensing apparatus 40. The example of the sensing apparatus 40 shown in FIG. 4 includes a flow cell 41 and the sensing system 10" integrated into the flow cell 41. It is to be understood that any example of the sensing system 10, 10', 10" may be used in the sensing apparatus 40.

The flow cell 41 is a vessel that contains the sensing system 10". It is to be understood that other vessels, such as a well, tube, channel, cuvette, Petri plate, bottle, or the like may alternatively contain the sensing system 10". Cyclic processes, such as nucleic acid sequencing reactions, are particularly well suited for flow cells 41.

Example flow cells 41 include a substrate/support 13 and a lid bonded 43 directly or indirectly thereto or integrally formed therewith. Flow cell 41 may include a fluid inlet 45 and a fluid outlet 47 that enable delivery of bulk reagents to one sensing system 10" or an array of sensing systems 10" contained within the flow cell 41. Any individual flow cell 41 may include tens, hundreds, thousands, millions, or even billions of individually addressable and readable sensing systems 10, 10', 10".

Figures 7A, 7B:
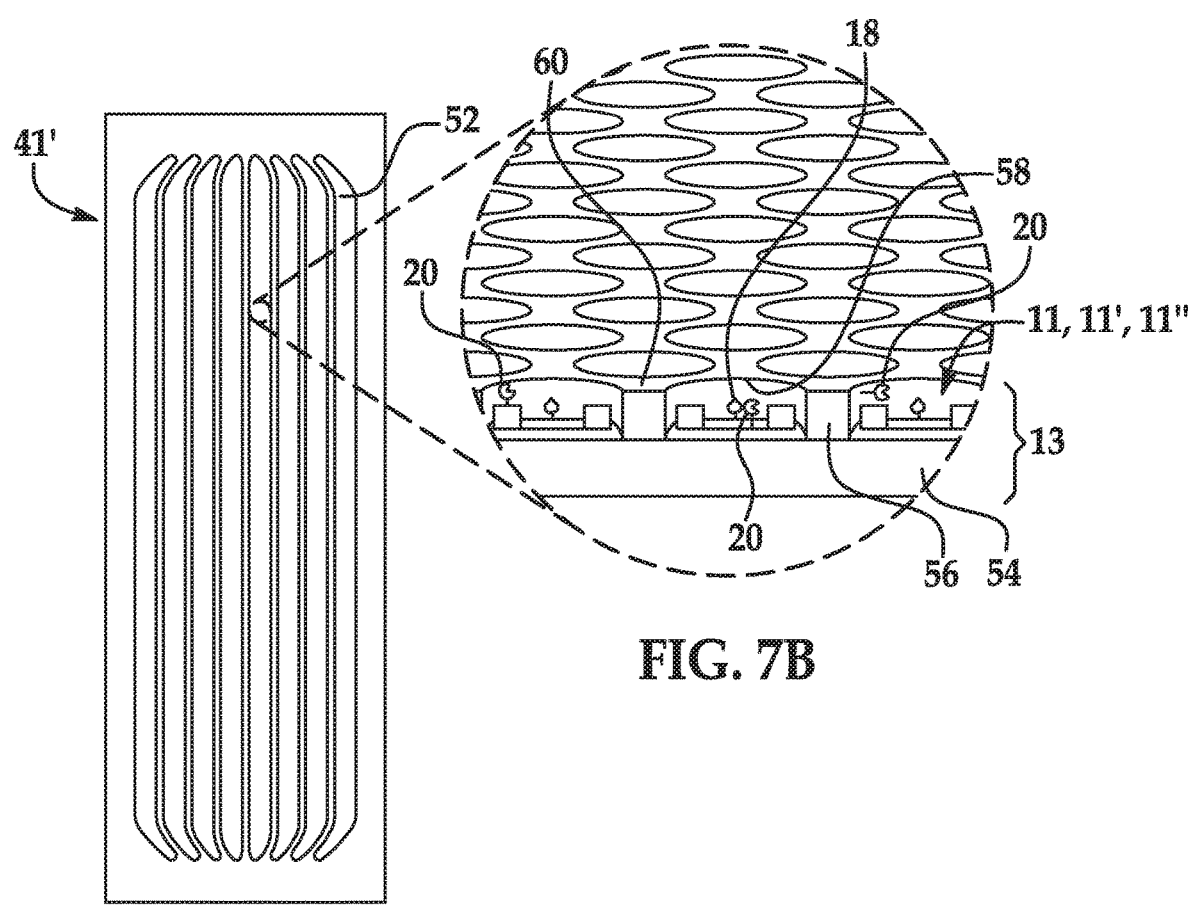
FIG. 7A is a top view of another example of a flow cell.
FIG. 7B is an enlarged, and partially cutaway view of an example of sensors positioned in the architecture of the flow cell of FIG. 7A.

The example shown in FIGS. 7A and 7B is one example of a flow cell 41' that includes an array of sensing systems 10, 10', 10". The array may include several sensing systems 10, 10', 10", each of which is positioned on a substrate and is configured with electronic circuitry so that it is individually addressable and readable. In an example, each sensing system 10, 10', 10" of the array may be positioned on the substrate in an individual depression. The depressions physically separate each of the sensing systems 10, 10', 10".

In the example of FIG. 7A, the flow cell 41' includes flow channels 52. While several flow channels 52 are shown, it is to be understood that any number of channels 52 may be included in the flow cell 41' (e.g., a single channel 52, four channels 52, etc.). Each flow channel 52 is an area defined between two bonded components (e.g., a substrate and a lid or two substrates), which can have fluids (e.g., those describe herein) introduced thereto and removed therefrom. Each flow channel 52 may be isolated from each other flow channel 52 so that fluid introduced into any particular flow channel 52 does not flow into any adjacent flow channel 52. Some examples of the fluids introduced into the flow channels 52 may introduce reaction components (e.g., labeled nucleotides 26, etc.), washing solutions, etc.

An example of the architecture within the flow channels 52 of the flow cell 41' is shown FIG. 7B. In the example shown in FIG. 7B, the flow cell 41' includes a substrate 13 including a support 54 and a patterned material 56 positioned on the support 54. The patterned material 56 defines depressions 58 separated by interstitial regions 60. In this example, a surface of the support 54 is exposed at each of the depressions 58, and a sensing system 10, 10', 10" is positioned within each depression 58.

The support 54 in FIG. 7B provides support for the other components of the flow cell 41'. The support 54 is generally rigid and is insoluble in an aqueous liquid. Examples of suitable supports 54 include epoxy siloxane, glass, modified glass, plastics, nylon, ceramics/ceramic oxides, silica (silicon oxide ($SiO_2$)), fused silica, silica-based materials, aluminum silicate, silicon, modified silicon (e.g., boron doped p+ silicon), silicon nitride ($Si_3N_4$), tantalum pentoxide ($TaO_5$) or other tantalum oxide(s) ($TaO_x$), hafnium oxide ($HaO_2$), inorganic glasses, or the like. Some examples of suitable plastics for the support 54 include acrylics, polystyrene, copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc. The support 54 may also be glass or silicon, with a coating layer of tantalum oxide or another ceramic oxide at the surface.

The form of the support 54 may be a wafer, a panel, a rectangular sheet, a die, or any other suitable configuration. In an example, the support 54 may be a circular wafer or panel having a diameter ranging from about 2 mm to about 300 mm. As a more specific example, the support 54 is a wafer having a diameter ranging from about 200 mm to about 300 mm. In another example, the support 54 may be a rectangular sheet or panel having its largest dimension up to about 10 feet (~3 meters). As a specific example, the support 54 is a die having a width ranging from about 0.1 mm to about 10 mm. While example dimensions have been provided, it is to be understood that a support 54 with any suitable dimensions may be used.

In the example shown in FIG. 7B, the patterned material 56 is positioned on the support 54. It is to be understood that any material that can be selectively deposited, or deposited and patterned to form the depressions 58 and the interstitial regions 60 may be used for the patterned material 56.

As one example, an inorganic oxide may be selectively applied to the support 66 via vapor deposition, aerosol printing, or inkjet printing. Examples of suitable inorganic oxides include tantalum oxide (e.g., $Ta_2O_5$), aluminum oxide (e.g., $Al_2O_3$), silicon oxide (e.g., $SiO_2$), hafnium oxide (e.g., $HfO_2$), etc.

As another example, a resin may be applied to the support 54 and then patterned. Suitable deposition techniques include chemical vapor deposition, dip coating, dunk coating, spin coating, spray coating, puddle dispensing, ultrasonic spray coating, doctor blade coating, aerosol printing, screen printing, microcontact printing, etc. Suitable patterning techniques include photolithography, nanoimprint lithography (NIL), stamping techniques, embossing techniques, molding techniques, microetching techniques, printing techniques, etc. Some examples of suitable resins include a polyhedral oligomeric silsesquioxane resin (POSS)-based resin, a non-POSS epoxy resin, a poly(ethylene glycol) resin, a polyether resin (e.g., ring opened epoxies), an acrylic resin, an acrylate resin, a methacrylate resin, an amorphous fluoropolymer resin (e.g., CYTOP® from Bellex), and combinations thereof.

As used herein, the term "polyhedral oligomeric silsesquioxane" (POSS) refers to a chemical composition that is a hybrid intermediate (e.g., $RSiO_{1.5}$) between that of silica ($SiO_2$) and silicone ($R_2SiO$). An example of POSS can be that described in Kehagias et al., Microelectronic Engineering 86 (2009), pp. 776-778, which is incorporated by reference in its entirety. In an example, the composition is an organosilicon compound with the chemical formula $[RSiO_{3/2}]_n$, where the R groups can be the same or different. Example R groups for POSS include epoxy, azide/azido, a thiol, a poly(ethylene glycol), a norbornene, a tetrazine, acrylates, and/or methacrylates, or further, for example, alkyl, aryl, alkoxy, and/or haloalkyl groups. The resin composition disclosed herein may comprise one or more different cage or core structures as monomeric units. The polyhedral structure may be a $T_8$ structure, such as:

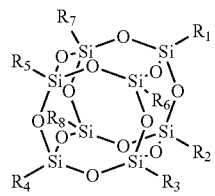

and represented by:

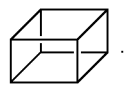   $T_8$

This monomeric unit typically has eight arms of functional groups $R_1$ through $R_8$.

The monomeric unit may have a cage structure with 10 silicon atoms and 10 R groups, referred to as $T_{10}$, such as:

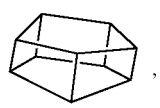   $T_{10}$ or may have a cage structure with 12 silicon atoms and 12 R groups, referred to as $T_{12}$, such as:

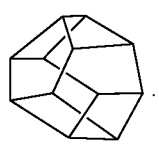   $T_{12}$

The POSS-based material may alternatively include $T_6$, $T_{14}$, or $T_{16}$ cage structures. The average cage content can be adjusted during the synthesis, and/or controlled by purification methods, and a distribution of cage sizes of the monomeric unit(s) may be used in the examples disclosed herein.

As shown in FIG. 7B, the patterned material 56 includes the depressions 58 defined therein, and interstitial regions 60 separating adjacent depressions 58. Many different layouts of the depressions 58 may be envisaged, including regular, repeating, and non-regular patterns. In an example, the depressions 58 are disposed in a hexagonal grid for close packing and improved density. Other layouts may include, for example, rectilinear (rectangular) layouts, triangular layouts, and so forth. In some examples, the layout or pattern can be an x-y format of depressions 58 that are in rows and columns. In some other examples, the layout or pattern can be a repeating arrangement of depressions 58 and/or interstitial regions 60. In still other examples, the layout or pattern can be a random arrangement of depressions 58 and/or interstitial regions 60. The pattern may include spots, pads, wells, posts, stripes, swirls, lines, triangles, rectangles, circles, arcs, checks, plaids, diagonals, arrows, squares, and/or cross-hatches.

The layout or pattern of the depressions 58 may be characterized with respect to the density of the depressions 58 (number of depressions 58) in a defined area. For example, the depressions 58 may be present at a density of approximately 2 million per $mm^2$. The density may be tuned to different densities including, for example, a density of about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more, or less. It is to be further understood that the density of depressions 58 in the patterned material 56 can be between one of the lower values and one of the upper values selected from the ranges above. As examples, a high density array may be characterized as having depressions 58 separated by less than about 100 nm, a medium density array may be characterized as having depressions 58 separated by about 400 nm to about 1 μm, and a low density array may be characterized as having depressions 58 separated by greater than about 1 μm. While example densities have been provided, it is to be understood any suitable densities may be used.

The layout or pattern of the depressions 58 may also or alternatively be characterized in terms of the average pitch, or the spacing from the center of the depression 58 to the center of an adjacent depression 58 (center-to-center spacing) or from the edge of one depression 58 to the edge of an adjacent depression 58 (edge-to-edge spacing). The pattern can be regular, such that the coefficient of variation around the average pitch is small, or the pattern can be non-regular in which case the coefficient of variation can be relatively large. In either case, the average pitch can be, for example, about 50 nm, about 0.1 μm, about 0.5 μm, about 1 μm, about 5 μm, about 10 μm, about 100 μm, or more or less. The average pitch for a particular pattern of depressions 58 can be between one of the lower values and one of the upper values selected from the ranges above. In an example, the depressions 58 have a pitch (center-to-center spacing) of about 1.5 μm. While example average pitch values have been provided, it is to be understood that other average pitch values may be used.

The size of each depression 58 may be characterized by its volume, depth, and/or diameter.

Each depression 58 can have any volume that is capable of confining a fluid. The minimum or maximum volume can be selected, for example, to accommodate the throughput (e.g., multiplexity), resolution, labeled nucleotides 26, or analyte reactivity expected for downstream uses of the flow cell 41'. For example, the volume can be at least about $1\times10^{-3}$ µm$^3$, at least about $1\times10^{-2}$ µm$^3$, at least about 0.1 µm$^3$, at least about 1 µm$^3$, at least about 10 µm$^3$, at least about 100 µm$^3$, or more. Alternatively or additionally, the volume can be at most about $1\times10^4$ µm$^3$, at most about $1\times10^3$ µm$^3$, at most about 100 µm$^3$, at most about 10 µm$^3$, at most about 1 µm$^3$, at most about 0.1 µm$^3$, or less.

The depth of each depression 58 can large enough to house one sensing system 10, 10', 10''. In an example, the depth may be at least about 1 µm, at least about 10 µm, at least about 100 µm, or more. Alternatively or additionally, the depth can be at most about $1\times10^3$ µm, at most about 100 µm, at most about 10 µm, or less. The depth of each depression 58 can be greater than, less than or between the values specified above.

In some instances, the diameter or length and width of each depression 58 can be at least about 50 nm, at least about 0.1 µm, at least about 0.5 µm, at least about 1 µm, at least about 10 µm, at least about 100 µm, or more. Alternatively or additionally, the diameter or length and width can be at most about $1\times10^3$ µm, at most about 100 µm, at most about 10 µm, at most about 1 µm, at most about 0.5 µm, at most about 0.1 µm, or less (e.g., about 50 nm). The diameter or length and width of each depression 58 can be greater than, less than or between the values specified above.

As depicted in FIG. 7B, each of the depressions 58 in the array includes a respective charge sensor 11, 11', 11''. It is desirable for each charge sensor 11, 11', 11'' in each depression 58 to have one charged molecule 18, 18' attached thereto, and to have one polymerase 20 attached within proximity thereof. In some examples, each depression 58 has one charge sensor 11, 11', 11'', one charged molecule 18, 18, and one polymerase 20 therein. In other examples, some depressions 58 have one charge sensor 11, 11', 11'', one charged molecule 18, 18, and one polymerase 20 therein; while other depressions 58 have one charge sensor 11, 11', 11'', one charged molecule 18, 18, and more than one polymerase 20 therein; and still other depressions 58 have one charge sensor 11, 11', 11'', one charged molecule 18, 18, and no polymerase 20 therein. In these examples, the number of polymerase(s) 20 become attached within any given depression 58 may be random and determined by the Poisson distribution.

In some examples, the charge sensor 11, 11', 11'' with the charged molecule 18, 18' attached thereto may be pre-assembled in the depressions 58. To attach the polymerases 20 within respective depressions 58, a fluid containing the polymerase 20 may be introduced to each lane 52 of the flow cell 41'. The polymerase 20 may include a tether 22 that attaches within a depression 58, or the linker 22 may be pre-attached within a depression 58 and the polymerase 20 can attach to the linker 22. The fluid may be allowed to incubate for a desirable time and at a desirable temperature to allow the polymerases 20 to attach.

As depicted in FIG. 7B, the polymerase 20 may attach to any component and/or any surface within the flow cell 41'. In some examples, the polymerase 20 is attached to an electrode 12 or 14, a surface of the substrate 13 (e.g., a bottom of the depression 58, a sidewall of the depression 58, etc.), on the electrically conductive channel 16, on the charged molecule 18, 18', etc.

Each of the charge sensors 11, 11', 11'' is individually electrically addressable and readable. As such, the signals resulting from charged molecule conformation changes taking place within each depression 58 may be individually detected and analyzed.

Any examples of the sensing apparatus 40 may also include a reagent delivery system 49 to selectively introduce a reagent to an input (e.g., fluid inlet(s) 45) of the flow cell 41 or a lane 52 of a flow cell 41', over the sensing system(s) 10, 10', 10'', and then out of the fluid outlet 47. The reagent delivery system 49 may include tubing or other fluidics that can permanently or removably attach to the fluid inlet 45. The reagent delivery system 49 may include a sample container 51. The reagent (including any example of labeled nucleotide 26 to be introduced to the sensing system 10'') may be stored in the sample container or prepared and introduced to the sample container just before use. The reagent deliver system 49 may also include a pump or other suitable equipment to retrieve the reagent from the sample container 51 and deliver it to the fluid inlet 45. In other examples, the sample container 51 is positioned so the reagent can flow by gravity to the fluid inlet 45, over the sensing system 10'', and out the fluid outlet 47.

The charge sensor 11, 11', 11'' in the flow cell 41, 41' may also be operatively connected to a detector 15 to detect conductance changes of the charge sensor 11, 11', 11'' when the sensing system 10, 10', 10'' and sensing apparatus 40 are used.

The sensing systems 10, 10', 10'' disclosed herein may be used in a sensing method. An example of the method is shown schematically in FIG. 5. The method includes:

introducing a template polynucleotide chain 48 to a sensing system 10, 10', 10'' including: a charge sensor 11, 11', 11'' including two electrodes 12, 14 and an electrically conductive channel 16 connecting the two electrodes 12, 14; a charged molecule 18, 18' attached to the electrically conductive channel 16, wherein the charged molecule 18, 18' includes a recognition site 28; and a polymerase 20 attached to the electrically conductive channel 16 or to the charged molecule 18, 18';

introducing reagents including labeled nucleotides 26 to the sensing system 10, 10', 10'', whereby a nucleotide 30 of one of the labeled nucleotides 26 associates with the polymerase 20 and a recognition site specific label 24 of the one of the labeled nucleotides 26 associates with the recognition site 28 to induce a conformational change of the charged molecule 18, 18'; and in response to the conformational change of the charged molecule 18, 18', detecting a response of the charge sensor 11, 11', 11''.

The template polynucleotide chain 48 may be any sample that is to be sequenced, and may be composed of DNA, RNA, or analogs thereof (e.g., peptide nucleic acids). The source of the template (or target) polynucleotide chain 48 can be genomic DNA, messenger RNA, or other nucleic acids from native sources. In some cases, the template polynucleotide chain 48 that is derived from such sources can be amplified prior to use in a method or system 40 herein. Any of a variety of known amplification techniques can be used including, but not limited to, polymerase chain reaction (PCR), rolling circle amplification (RCA), multiple displacement amplification (MDA), or Recombinase Polymerase amplification (RPA). It is to be understood that amplification of the template polynucleotide chain 48 prior to use in the method or system 40 set forth herein is optional. As such, the template polynucleotide chain 48 will not be amplified prior to use in some examples. Template/target polynucleotide chains 48 can optionally be derived from synthetic libraries. Synthetic nucleic acids can have native DNA or RNA compositions or can be analogs thereof.

Biological samples from which the template polynucleotide chain 48 can be derived include, for example, those from a mammal, such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii, Takifugu rubripes*, yeast, *Saccharamoyces cerevisiae* or *Schizosaccharomyces pombe*; or a *Plasmodium falciparum*. Template polynucleotide chains 48 can also be derived from prokaryotes such as a bacterium, *Escherichia coli*, staphylococci or *Mycoplasma pneumoniae*; an archae; a virus such as Hepatitis C virus, ebola virus or human immunodeficiency virus; or a viroid. Template polynucleotide chains 48 can be derived from a homogeneous culture or population of the above organisms or alternatively from a collection of several different organisms, for example, in a community or ecosystem.

Moreover, template polynucleotide chains 48 may not be derived from natural sources, but rather can be synthesized using known techniques. For example, gene expression probes or genotyping probes can be synthesized and used in the examples set forth herein.

In some examples, template polynucleotide chains 48 can be obtained as fragments of one or more larger nucleic acids. Fragmentation can be carried out using any of a variety of techniques known in the art including, for example, nebulization, sonication, chemical cleavage, enzymatic cleavage, or physical shearing. Fragmentation may also result from use of a particular amplification technique that produces amplicons by copying only a portion of a larger nucleic acid chain. For example, PCR amplification produces fragments having a size defined by the length of the nucleotide sequence on the original template that is between the locations where flanking primers hybridize during amplification. The length of the template polynucleotide chain 48 may be in terms of the number of nucleotides or in terms of a metric length (e.g., nanometers).

A population of template/target polynucleotide chains 48, or amplicons thereof, can have an average strand length that is desired or appropriate for a particular application of the methods or system 40 set forth herein. For example, the average strand length can be less than about 100,000 nucleotides, about 50,000 nucleotides, about 10,000 nucleotides, about 5,000 nucleotides, about 1,000 nucleotides, about 500 nucleotides, about 100 nucleotides, or about 50 nucleotides. Alternatively or additionally, the average strand length can be greater than about 10 nucleotides, about 50 nucleotides, about 100 nucleotides, about 500 nucleotides, about 1,000 nucleotides, about 5,000 nucleotides, about 10,000 nucleotides, about 50,000 nucleotides, or about 100,000 nucleotides. The average strand length for a population of target polynucleotide chains 48, or amplicons thereof, can be in a range between a maximum and minimum value set forth above.

In some cases, a population of template/target polynucleotide chains 48 can be produced under conditions or otherwise configured to have a maximum length for its members. For example, the maximum length for the members can be less than about 100,000 nucleotides, about 50,000 nucleotides, about 10,000 nucleotides, about 5,000 nucleotides, about 1,000 nucleotides, about 500 nucleotides, about 100 nucleotides or about 50 nucleotides. Alternatively or additionally, a population of template polynucleotide chains 48, or amplicons thereof, can be produced under conditions or otherwise configured to have a minimum length for its members. For example, the minimum length for the members can be more than about 10 nucleotides, about 50 nucleotides, about 100 nucleotides, about 500 nucleotides, about 1,000 nucleotides, about 5,000 nucleotides, about 10,000 nucleotides, about 50,000 nucleotides, or about 100,000 nucleotides. The maximum and minimum strand length for template polynucleotide chains 48 in a population can be in a range between a maximum and minimum value set forth above.

As shown in FIG. 5, the template polynucleotide chain 48 introduced to the sensing system 10 (or 10', 10") may be held in place by the polymerase 20, which, in this example, is tethered to the electrically conductive channel 16. The template polynucleotide chain 48 shown in FIG. 5 is a template strand of DNA. The template polynucleotide chain 48 may be introduced in a biologically stable solution, along with reagents, such as the labeled nucleotides 26. The biologically stable solution may be any buffer suitable for polymerase base incorporation reactions, such as polymerase chain reaction (PCR) or linear amplification. As an example, biologically stable solution may include a buffer having a pH near 7, a salt concentration above several millimolar, and $Mg^{2+}$ ions at millimolar concentration.

Also as shown in FIG. 5, the labeled nucleotide 26 may include a base that is complementary to a target nucleic acid of the template polynucleotide chain 48. The labeled nucleotide 26 will be held in place, in part, by the polymerase 20 that is also bound to the template polynucleotide chain 48. As an example, the polymerase 20 may incorporate a particular nucleotide 30, the nucleotide 30 may be held for a time period ranging from a few (e.g., 2) milliseconds to a few hundreds of milliseconds.

The interaction between the labeled nucleotide 26 and polymerase 20 and the length of the linking molecule 32 enable the target label 24 to associate within proximity of the charged molecule 18. When the sensing systems 10, 10', 10" are present in an array and include individually addressable and individually readable charge sensors 11, 11', 11", it is to be understood that the length of the linking molecule 32 may also prohibit any individual target label 24 from associating with an adjacent sensing system 10, 10', 10" once the labeled nucleotide 26 interacts with the polymerase 20 of a particular sensing system 10, 10', 10".

In some examples, the association of the target label 24 causes the effective concentration of the label 24 to increase, causing the charged molecule 18 to bind to the target label 24. The charged molecule 18 may dynamically change its conformation at equilibrium, and in the absence of the target label 24, may spend a majority of the time in one specific conformation (i.e., the unbound favored conformation). Binding of the target label 24 will cause the charged molecule 18 to move to a different favored conformation (from the unbound favored conformation). The favored conformation during binding is different from the unbound favored conformation (e.g., the conformation most exhibited by the charged molecule 18 in the absence of the bound label 24). The charge distribution in the unbound favored conformation is different from the charge distribution in the favored conformation (e.g., when the charged molecule 18 is bound to label 24). The change in charge distribution of the charged molecule 18, in turn, alters the conductance in the channel 16.

The response of the charge sensor 11, 11', 11" may be indicative of the incorporated base of the labeled nucleotide 26 because the target label 24 is nucleotide-specific (i.e., a specific label 24 is selected for a specific base) and because the recognition site 28 of the charged molecule 18 is label-specific. As such, the method may also involve associating the response of the charge sensor 11, 11', 11" with the associated recognition site specific label 24 (i.e., the label 24 that has altered the conformation of the charged molecule 18), and based on the associated recognition site specific label 24, identifying the nucleotide (e.g., the base) of the associated labeled nucleotide 26 (i.e., the labeled nucleotide 26 that has associated with the polymerase 20 and the recognition site 28).

It is to be understood that the on- and off-rates between the charged molecule(s) 18, 18' and the label(s) 24 can be adjusted so that unique fingerprint signals are generated.

For labels 24 with slow off-rates, the label 24 will remain bound for a significant duration, for example, during the entire nucleotide incorporation cycle. This extended binding will produce changes in the DC level of the current going through the channel 16 of the charge sensor 11, 11'. This is illustrated schematically in FIG. 6A, where different labels 24 with slow off-rates are used for the four different nucleotides, resulting in four different and distinct detectable signals. These signals could be detected through a single charged molecule 18, 18' with four different recognition sites 28, or through up to four different charged molecules 18, 18', each with a label-specific recognition site 28, or through a single charged molecule 18, 18' with a single recognition site 28 that can bind up to four different nucleotides at distinct slow off-rates.

For labels 24 with fast on- and off-rates, the label 24 can associate/disassociate from the charged molecule 18, 18' multiple times during the entire nucleotide incorporation cycle. This rapid on and off binding will produce chatter-like signals (e.g., DC level, amplitude, frequency, percentile levels, characteristic distribution, etc.) from the charge sensor 11, 11'. This is illustrated schematically in FIG. 6B, where different labels 24 with fast on- and off-rates are used for the four different nucleotides, resulting in four different and distinct detectable signals. These signals could be detected through a single charged molecule 18, 18' with four different recognition sites 28, or through up to four different charged molecules 18, 18', each with a label-specific recognition site 28, or through a single charged molecule 18, 18' with a single recognition site 28 that can bind from one up to four different nucleotides at distinct on- and off-rates.

The frequency at which the conformational state of the charged molecule 18, 18' is changed may also be monitored.

The magnitude of the charge sensor responses may also be distinct. In some examples, the recognition site 28 is to reversibly bind up to four different labeled nucleotides 26. When one of the four different labeled nucleotides 26 is associated with the polymerase 20 and the recognition site 28, the response of the charge sensor 11, 11', 11" has a distinct magnitude that can be used to identify the one of the four different labeled nucleotides 26. Each of the four different labeled nucleotides 26 may also have a distinct magnitude (e.g., a magnitude that is different from the magnitudes associated with each of the other four different labeled nucleotides 26).

Figure 6A:
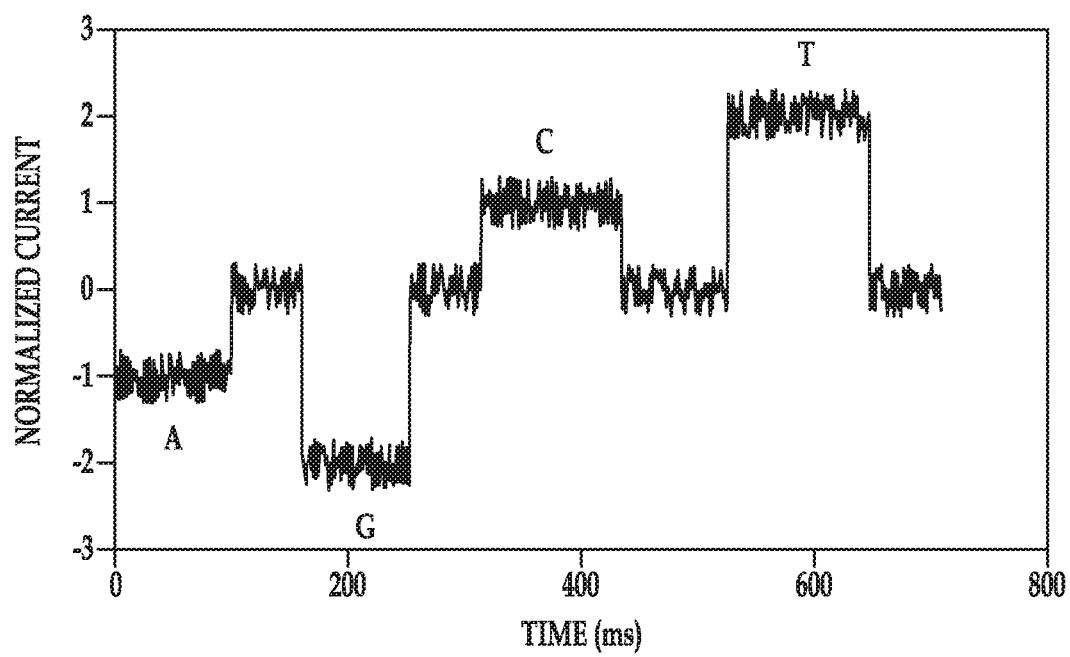
FIGS. 6A and 6B are graphs illustrating potential responses of the sensors disclosed herein.
Figure 6B:
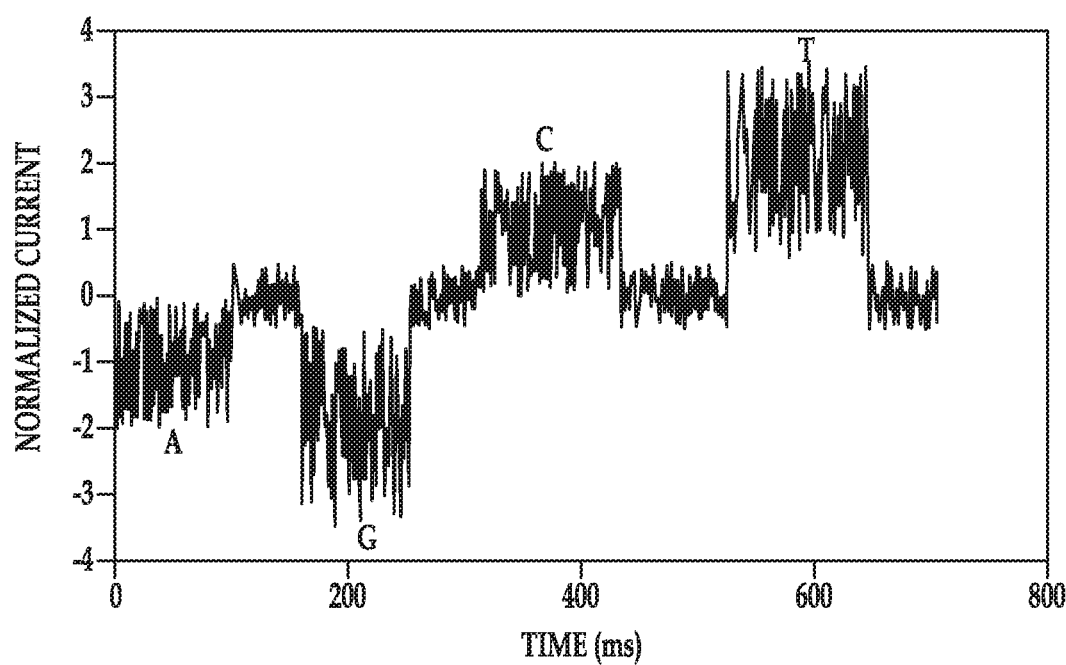

In other examples, the modalities from FIGS. 6A and 6B may be combined in some form. For example, in a plurality of labeled nucleotides 26 exposed to the sensing system 10, 10', 10", some labels 24 may be used that have slow on- and off-rates and other labels 24 may be used that have fast on- and off-rates.

As a result of the incorporation cycle described herein, the base of the associated labeled nucleotide 26 will be incorporated into a nascent strand 50 that is hybridized to the template polynucleotide chain 48. When the base is fully incorporated and the sugar backbone of the nascent strand 50 is extended, the linker 32 between the nucleotide 30 and the label 24 is naturally cleaved. This results in a reduction of the effective concentration of the label 24 back to background levels. The target label 24 dissociates and the changed molecule 18, 18' returns to its unbound (sometimes referred to as "wild type") conformation, where it preferentially exhibits the favored unbound conformation.

The method disclosed herein may be repeated for a desired number of sequencing cycles.

The labeled nucleotides 26 and sensing systems 10, 10', 10" disclosed herein may be used for any of a variety of applications. As described in reference to FIG. 5, a particularly useful application is nucleic acid sequencing, such as sequencing-by-synthesis (SBS). In SBS, extension of a nucleic acid sequencing primer along a template nucleic acid 48 is monitored to determine the sequence of nucleotides in the template. The underlying chemical process can be polymerization (e.g., as catalyzed by a polymerase enzyme 20 as described herein). In a particular polymerase-based SBS example, nucleotides (e.g., bases) are added to a sequencing primer (thereby extending the sequencing primer) in a template dependent fashion such that detection of the order and type of nucleotides added to the primer to form a nascent strand can be used to determine the sequence of the template. A plurality of different templates 48 at different sensing systems 10, 10', 10" of an array can be subjected to an SBS technique. Events occurring at different templates 48 can be distinguished, in part, because of the location of the specific sensing system 10, 10', 10" in the array. The charge sensors 11, 11' of each sensing system 10, 10', 10" in the array may be individually addressable and readable, and thus signals at each sensor 11, 11' can be detected.

Other suitable applications for the labeled nucleotides 26 and sensing systems 10, 10', 10" disclosed herein include sequencing-by-ligation and sequencing-by-hybridization.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Furthermore, it is to be understood that the ranges provided herein include the stated range and any value or sub-range within the stated range, as if they were explicitly recited. For example, a range represented by from 1 nm to less than 1 µm, should be interpreted to include not only the explicitly recited limits of from 1 nm to less than 1 µm, but also to include individual values, such as about 15 nm, 22.5 nm, 45 nm, etc., and sub-ranges, such as from about 20 nm to about 48 nm, etc.

While several examples have been described in detail, it is to be understood that the disclosed examples may be modified. Therefore, the foregoing description is to be considered non-limiting.

What is claimed is:

1. A sensing system, comprising:
   a charge sensor including:
     two electrodes; and
     an electrically conductive channel connecting the two electrodes;
   a polymerase attached to the electrically conductive channel through a first tether, the polymerase to hold a template polynucleotide chain that is to be sequenced; and
   a charged molecule that is separate and distinct from the polymerase, the charged molecule being attached i) directly to the electrically conductive channel or indirectly to the electrically conductive channel through a second tether and ii) within a distance of about 5 nm to about 50 nm of the polymerase, wherein the charged molecule:
     includes a recognition site to reversibly bind a label of a labeled nucleotide that is being incorporated into the template polynucleotide chain, wherein the label is selected from the group consisting of an antibiotic, an amino acid, and a small molecule selected from the group consisting of theophylline, dopamine, sulforhodamine, and cellobiose;
     has an unbound favored conformation associated with an unbound charge configuration;
     has a favored conformation associated with a charge configuration when the recognition site is bound to the label, wherein the charge configuration is different from the unbound charge configuration; and
     is a charged aptamer selected from the group consisting of a DNA aptamer, an RNA aptamer, and an analog thereof.

2. The sensing system as defined in claim 1, wherein:
   the charged molecule:
     further includes a second recognition site to reversibly bind a second label of a second labeled nucleotide and has a second favored conformation associated with a second charge configuration when the second recognition site is bound to the second label;
     further includes a third recognition site to reversibly bind a third label of a third labeled nucleotide and has a third favored conformation associated with a third charge configuration when the third recognition site is bound to the third label; and
     further includes a fourth recognition site to reversibly bind a fourth label of a fourth labeled nucleotide and has a fourth favored conformation associated with a fourth charge configuration when the fourth recognition site is bound to the fourth label; and
   the unbound favored conformation associated with the unbound charge configuration occurs when each of the recognition site, the second recognition site, the third recognition site, and the fourth recognition site is unbound.

3. The sensing system as defined in claim 1, further comprising:
   a second charged molecule attached to the electrically conductive channel, wherein the second charged molecule:
     includes a second recognition site to reversibly bind a second label of a second labeled nucleotide;
     has a second charged molecule unbound favored conformation associated with a second charged molecule unbound charge configuration; and
     has a second charged molecule favored conformation associated with a second charged molecule charge configuration when the second recognition site is bound to the second label.

4. The sensing system as defined in claim 3, further comprising:
   a third charged molecule attached to the electrically conductive channel, wherein the third charged molecule:
     includes a third recognition site to reversibly bind a third label of a third labeled nucleotide;
     has a third charged molecule unbound favored conformation associated with a third charged molecule unbound charge configuration; and
     has a third charged molecule favored conformation associated with a third charged molecule charge configuration when the third recognition site is bound to the third label; and
   a fourth charged molecule attached to the electrically conductive channel, wherein the fourth charged molecule:
     includes a fourth recognition site to reversibly bind a fourth label of a fourth labeled nucleotide;
     has a fourth charged molecule unbound favored conformation associated with a fourth charged molecule unbound charge configuration; and
     has a fourth charged molecule favored conformation associated with a fourth charged molecule charge configuration when the fourth recognition site is bound to the fourth label.

5. The sensing system as defined in claim 1, wherein:
   the charged molecule further includes a second recognition site to reversibly bind a second label of a second labeled nucleotide and has a second favored conformation associated with a second charge configuration when the second recognition site is bound to the second label; and
   the sensing system further comprises a second charged molecule attached to the electrically conductive channel, wherein the second charged molecule:
     includes:
       a third recognition site to reversibly bind a third label of a third labeled nucleotide; and
       a fourth recognition site to reversibly bind a fourth label of a fourth labeled nucleotide;
     has a second charged molecule unbound favored conformation associated with a second charged molecule unbound charge configuration;
     has a third favored conformation associated with a third charge configuration when the third recognition site is bound to the third label; and
     has a fourth favored conformation associated with a fourth charge configuration when the fourth recognition site is bound to the fourth label.

6. The sensing system as defined in claim 1, wherein the charged molecule further includes a second recognition site to reversibly bind a second label of the labeled nucleotide.

7. The sensing system as defined in claim 1, wherein:
the charged molecule is the DNA aptamer or the RNA aptamer;
the DNA aptamer or the RNA aptamer is a thiolated aptamer; and
the electrically conducting channel includes an amine terminated silane that is bound to the thiolated aptamer.

8. The sensing system as defined in claim 1, wherein the first and second tethers are separate poly(ethylene glycol) chains.

9. A sensing apparatus, comprising:
a flow cell; and
a sensing system integrated into the flow cell, the sensing system including:
    a charge sensor including an electrically conductive channel;
    a polymerase attached to the electrically conductive channel through a first tether, the polymerase to hold a template polynucleotide chain that is to be sequenced; and
    a charged molecule that is separate and distinct from the polymerase, the charged molecule being i) directly attached to the electrically conductive channel or indirectly attached to the electrically conductive channel through a second tether and ii) within a distance of about 5 nm to about 50 nm of the polymerase, wherein the charged molecule:
        has an unbound favored conformation associated with an unbound charge configuration;
        has a favored conformation associated with a charge configuration when a recognition site of the charged molecule is bound to a label of a labeled nucleotide that is being incorporated into the template polynucleotide chain, wherein the charge configuration is different from the unbound charge configuration, and wherein the label is selected from the group consisting of an antibiotic, an amino acid, and a small molecule selected from the group consisting of theophylline, dopamine, sulforhodamine, and cellobiose; and
        is a charged aptamer selected from the group consisting of a DNA aptamer, an RNA aptamer, and an analog thereof.

10. The sensing apparatus as defined in claim 9, further comprising a reagent delivery system to introduce a reagent to an input of the flow cell.

11. The sensing apparatus as defined in claim 10, wherein the reagent is in a sample container, the reagent including the labeled nucleotide, which includes:
a nucleotide;
a linking molecule attached to a phosphate group of the nucleotide; and
the label attached to the linking molecule.

12. The sensing apparatus as defined in claim 9, further comprising a detector to detect a response from the charge sensor.

13. A method, comprising:
introducing the template polynucleotide chain that is to be sequenced to the sensing system of claim 1, whereby the polymerase holds the template polynucleotide chain;
introducing reagents including labeled nucleotides to the sensing system, whereby the polymerase incorporates a nucleotide of one of the labeled nucleotides into the template polynucleotide chain, and the label of the one of the labeled nucleotides reversibly binds with the recognition site while the nucleotide is incorporated, which induces a conformational change of the charged molecule; and
in response to the conformational change of the charged molecule, detecting a response of the charge sensor.

14. The method as defined in claim 13, further comprising:
associating the response of the charge sensor with the label; and
based on the label, identifying the nucleotide of the one of the labeled nucleotides.

15. The method as defined in claim 13, wherein the charged molecule includes a plurality of different recognition sites, each of which is to reversibly bind a different label of a different labeled nucleotide at a distinct rate.

16. The method as defined in claim 15, further comprising:
detecting a plurality of responses of the charge sensor in response to different conformational changes of the charged molecule when different labeled nucleotides respectively associate with the polymerase and different labels of the different labeled nucleotides respectively bind to the plurality of different recognition sites; and
identifying each respectively associated different labeled nucleotide by the distinct rate.

17. The method as defined in claim 13, wherein the recognition site is to reversibly bind a plurality of different labels of a plurality of different labeled nucleotides at a plurality of distinct rates, and wherein the method further comprises:
detecting a plurality of responses of the charge sensor in response to different conformational changes of the charged molecule when at least some of the different labeled nucleotides respectively associate with the polymerase and at least some of the different labels respectively bind to the recognition site; and
identifying the at least some of the respectively associated different labeled nucleotides by the plurality of distinct rates.

18. The method as defined in claim 13, wherein the recognition site is to reversibly bind up to four different labeled nucleotides, and wherein the method further comprises:
detecting up to four different responses of the charge sensor in response to different conformational changes of the charged molecule when the up to four different labeled nucleotides respectively associate with the polymerase and the recognition site, wherein each of the up to four different responses has a distinct magnitude; and
identifying each of the up to four respectively associated different labeled nucleotide by the distinct magnitude.

* * * * *

UNITED STATES PATENT AND TRADEMARK OFFICE
CERTIFICATE OF CORRECTION

| | |
|---|---|
| PATENT NO. | : 11,782,006 B2 |
| APPLICATION NO. | : 16/701747 |
| DATED | : October 10, 2023 |
| INVENTOR(S) | : Boyanov et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 636 days.

Signed and Sealed this
First Day of July, 2025

Coke Morgan Stewart
*Acting Director of the United States Patent and Trademark Office*